United States Patent
Kates et al.

(10) Patent No.: US 12,156,883 B2
(45) Date of Patent: Dec. 3, 2024

(54) BISPHOSPHOCIN GEL FORMULATIONS AND USES THEREOF

(71) Applicant: Lakewood Amedex, Inc., Sarasota, FL (US)

(72) Inventors: Steven A. Kates, Needham, MA (US); Keith Arthur Johnson, Durham, NC (US)

(73) Assignee: Lakewood Amedex, Inc., University Park, FL (US)

( * ) Notice: Subject to any disclaimer, the term of this patent is extended or adjusted under 35 U.S.C. 154(b) by 0 days.

(21) Appl. No.: 17/396,989

(22) Filed: Aug. 9, 2021

(65) Prior Publication Data

US 2021/0361689 A1      Nov. 25, 2021

Related U.S. Application Data

(63) Continuation of application No. 16/006,660, filed on Jun. 12, 2018, now Pat. No. 11,096,954.

(60) Provisional application No. 62/518,262, filed on Jun. 12, 2017.

(51) Int. Cl.
| | |
|---|---|
| A61K 31/7072 | (2006.01) |
| A61K 9/00 | (2006.01) |
| A61K 9/06 | (2006.01) |
| A61K 47/10 | (2017.01) |
| A61K 47/34 | (2017.01) |
| A61P 17/00 | (2006.01) |
| A61P 31/04 | (2006.01) |

(52) U.S. Cl.
CPC ........ *A61K 31/7072* (2013.01); *A61K 9/0014* (2013.01); *A61K 9/06* (2013.01); *A61K 47/10* (2013.01); *A61K 47/34* (2013.01); *A61P 17/00* (2018.01); *A61P 31/04* (2018.01)

(58) Field of Classification Search
CPC .... A61K 31/7072; A61K 47/10; A61K 47/34; A61K 9/06; A61K 9/0014; A61P 17/00; A61P 31/04
See application file for complete search history.

(56) References Cited

U.S. PATENT DOCUMENTS

| | | | |
|---|---|---|---|
| 4,421,769 A | 12/1983 | Dixon et al. | |
| 4,963,555 A * | 10/1990 | Jones | A61K 9/0014 514/263.38 |
| 5,167,950 A | 12/1992 | Lins | |
| 5,208,015 A | 5/1993 | Shah | |
| 5,266,310 A | 11/1993 | Mundorf | |
| 5,660,839 A | 8/1997 | Allec et al. | |
| 5,824,666 A | 10/1998 | Deckner et al. | |
| 6,521,213 B1 | 2/2003 | Mautone | |
| 7,868,162 B2 | 1/2011 | Dale | |
| 8,598,129 B2 * | 12/2013 | Manetta | A61K 31/35 514/30 |
| 8,895,542 B2 | 11/2014 | Sulur et al. | |
| 2002/0032164 A1 | 3/2002 | Dale et al. | |
| 2005/0232891 A1 | 10/2005 | Moloney et al. | |
| 2007/0053971 A1 | 3/2007 | Dale | |
| 2011/0135713 A1 | 6/2011 | Dale | |
| 2011/0217358 A1 | 9/2011 | Feleki et al. | |
| 2016/0271217 A1 | 9/2016 | Grönberg et al. | |
| 2019/0046441 A1 | 2/2019 | Buge et al. | |

FOREIGN PATENT DOCUMENTS

| | | |
|---|---|---|
| CN | 1687100 | 10/2005 |
| EP | 0042827 A2 | 12/1981 |
| EP | 4241769 A2 | 9/2023 |
| JP | H01102029 A | 4/1989 |
| JP | H05194219 A | 8/1993 |
| JP | H0840870 A | 2/1996 |
| JP | 2010508280 A | 3/2010 |
| JP | 2011529098 A | 12/2011 |
| KR | 20120023653 A | 3/2012 |
| WO | 2010012720 A1 | 2/2010 |
| WO | 201755295 A1 | 4/2017 |

OTHER PUBLICATIONS

Valanne, S et al. CAMP factor homologues in Propionibacterium acnes: a new protein family differentially expressed by types I and II. Microbiology, vol. 151, May 1, 2005, pp. 1369-1379.
Jagtap, NS et al. Development and Evaluation of Herbal Wound Healing Formulations. International Journal of PharmTech Research, vol. 1, No. 4, Oct-Dec. 2009, pp. 1104-1108.
Moura, Lif et al. Recent advances on the development of wound dressings for diabetic foot ulcer treatment—A review. Acta Biomaterialia, vol. 9, No. 7, Jul. 2013, pp. 7093-7114.
Wagh, VD et al. Formulation and Evaluation of in situ Gel Drug Delivery System of Sesbania grandiflora Flower Extract for the Treatment of Bacterial Conjunctivitis. Journal of Pharmaceutical Sciences and Research, vol. 4, No. 8, 2012, pp. 1880-1884.
Aksungur, P et al. Chitosan delivery systems for the treatment of oral mucositis: in vitro and in vivo studies. Journal of Controlled Release, vol. 98, No. 2, Aug. 11, 2004, pp. 269-279.
Feng, X et al. Efficacy and tolerability of amorolfine 5% nail lacquer in combination with systemic antifungal agents for onychomycosis: A meta-analysis and systematic review. Dermatologic Therapy, vol. 30, No. 3, Jan. 18, 2017, e12457, pp. 1-6.
International Searching Authority, Patent Cooperation Treaty International Search Report and Written Opinion for International Application No. PCT/US2018/037151, Aug. 28, 2018.
Extended European Search Report; European Patent Office; EP Application No. 18816615.1; Feb. 5, 2021; 7 pages.
Office Action; Japanese Patent Office; Japanese Application No. 2019-567981; Jul. 16, 2021; 6 pages.

(Continued)

*Primary Examiner* — Jonathan S Lau

(74) *Attorney, Agent, or Firm* — Taft Stettinius & Hollister LLP

(57) ABSTRACT

Gel formulations having antimicrobial activity are disclosed. Methods of using the gel formulation are further disclosed.

23 Claims, No Drawings

(56) References Cited

OTHER PUBLICATIONS

Office Action; Korean Intellectual Property Office; Korean Application No. 10-2020-7000424; Oct. 7, 2021; 9 pages.

Non-Final Office Action; Brazilian Patent and Trademark Office; Brazilian Application No. BR 122021011439-0; Sep. 21, 2021; 13 pages.

International Preliminary Report on Patentability; The International Bureau of WIPO; International Application No. PCT/US2018/037151; Dec. 17, 2019; 12 pages,.

Indian Patent Office, Examination Report issued in corresponding Application No. 201927053712, dated Jun. 17, 2021, 7 pp.

Japanese Patent Office, Office Action issued in corresponding Application No. 2019-567981, mailed Feb. 4, 2022, 4 pp.

Mexican Patent Office, Office Action issued in corresponding Application No. MX/a/2019/014772, dated Apr. 4, 2022 with English translation, 8 pp.

Rowe, R et al., Handbook of Pharmaceutical Excipients, 6th ed., 2009, pp. 536-541 and pp. 549-553, http://repositorio.ub.edu.ar/handle/123456789/5143.

Lu et al., Handbook of Non-Invasive Drug Delivery Systems, 2010, Elsevier Inc., Chapter 3, "Emulsions and Microemulsions for Topical and Transdermal Drug Delivery," pp. 59-94.

Korean Patent Office, Non-Final Office Action, Korean Application No. 10-2020-7000424, dated Oct. 7, 2021, with English translation, 9 pp.

Chinese Patent Office, Non-Final Office Action, Chinese Application No. 201880038759.5, dated Oct. 26, 2022, with English translation 15 pp.

Mexican Patent Office, Non-Final Office Action, Chinese Application No. 201880038759.5, dated Oct. 26, 2022, with English translation 15 pp.

Brazilian Patent Office, Office Action, Brazilian Application No. 122021011439-0, dated Sep. 21, 2021, with English translation, 13 pp.

Extended European Search Report, European Patent Office, European Patent Application No. 23156658.9, Oct. 11, 2023, 6 pages.

Japanese Office Action, Japanese Patent Application No. 2022-147051, mailed Sep. 5, 2023.

Eccleston, G.M., "Multiple-phase oil-in-water emulsion," 1990 J. Soc. Cosmet. Chem., vol. 41, p. 1-22.

Australian Government, Examination report No. 1 for AU Application 2022224829, mailed Nov. 30, 2023.

* cited by examiner

BISPHOSPHOCIN GEL FORMULATIONS AND USES THEREOF

CROSS REFERENCE TO RELATED APPLICATIONS

This application is a continuation of U.S. patent application Ser. No. 16/006,660 filed on Jun. 12, 2018, which claims priority to U.S. Provisional Patent Application Ser. No. 62/518,262 filed on Jun. 12, 2017, each of which is incorporated by reference herein in its entirety.

FIELD

The present disclosure relates generally to gel formulations of deoxyribose-based therapeutics. The formulations of some embodiments of the present disclosure are particularly useful for the topical treatment of microbial infections.

BACKGROUND

Pathogenic microbial infections of the skin and other soft tissues cause a wide range of diseases. Epicutaneous bacterial infections are of particular concern and are responsible for a large number of serious diseases. The increasingly widespread prevalence of antibiotic-resistant bacterial strains, such as methicillin-resistant *Staphylococcus aureus* (MRSA), poses a growing health threat in the United States and elsewhere in the world. Despite significant efforts over the past few decades, the discovery of new antibiotics has proven to be exceedingly difficult, resulting in a steady decline in viable therapeutic options as bacteria become more resistant to existing antibiotics.

The treatment of Gram-negative bacterial infections is particularly challenging due to the lack of efficacious agents and the increasing incidence of drug resistant strains. Gram-negative bacteria are known to cause serious and sometimes life-threatening skin and soft tissue infections (SSTIs) including wound or surgical site infections. Gram-negative bacteria are often resistant to most or all of the currently available drugs.

Biofilms may also play a role in the most serious SSTIs. Biofilms are currently estimated to be responsible for over 65% of nosocomial infections and 80% of all microbial infections. Treating biofilm-mediated infections has proven to be very difficult because the typical minimum inhibitory concentrations (MICs) and the minimum bactericidal concentrations (MBCs) for biofilm bacterial cells are typically 10-1000 times higher than planktonic bacterial cells.

A new class of antibiotics called "Bisphosphocins" has been discovered that may offer an approach to treating a wide range of clinically important bacterial infections, including those caused by multidrug-resistant bacteria. Members of the Bisphosphocin class are characterized by a core deoxyribose unit having two protected phosphate groups. These molecules are highly protonated/acidified and exhibit excellent chemical stability, low pH resistance, and resistance to degradation by nucleases. The class of Bisphosphocins has been described as having antimicrobial activity. As antibiotics, it is believed that Bisphosphocins act by rapidly disrupting the bacterial cell membrane and/or cell wall in many different bacterial strains, including Gram-positive, Gram-negative, and certain antibiotic resistant strains. The most advanced member of the Bisphosphocin class, Nu-3, is currently undergoing clinical trials for treating infected diabetic foot ulcers.

The formulation of Nu-3 currently being used in clinical trials is an aqueous solution. Use of this formulation to treat diabetic foot ulcers has proven to be challenging. A more adherent topical formulation of Nu-3 and other Bisphosphocins would be desirable for several reasons. A more viscous formulation, like a gel, in particular, would be easier and more convenient to apply, aesthetically pleasing, and would allow for longer topical exposure times. Preparing a gel formulation for the Bisphosphocin class of compounds has been particularly difficult for several reasons. Because of their reduced level of activity when formulated at higher (more basic) pH levels, Bisphosphocins and their corresponding salts are typically formulated at highly acidic pH in the range of pH 1 to pH 5. For example, Bisphosphocins such as Nu-3 need to be formulated at pH 2 or below to retain the most potent antimicrobial activity.

In addition, topical formulations containing relatively high concentrations of the active Bisphosphocin compounds are desired but have also been difficult to make. Additionally, because the Bisphosphocins and their salts are strongly ionic, it has been difficult to use ionic polymers or emulsifying agents with these compounds. Thus, the resulting formulations are unstable and display poor cohesive properties.

Therefore, there is a need for new antimicrobial Bisphosphocin formulations that overcome the difficulties described above.

SUMMARY

The present disclosure provides gel formulations and uses thereof that address the challenges detailed above.

An aspect of the present disclosure provides a gel formulation. In some embodiments, the gel formulation includes a Bisphosphocin selected from the group consisting of Nu-2, Nu-3, Nu-4, Nu-5, and Nu-8, or a pharmaceutically acceptable salt thereof, or any combination thereof; a fatty alcohol thickening agent; and a nonionic polymer emulsifier. In some embodiments, the Bisphosphocin is Nu-3, or a pharmaceutically acceptable salt thereof.

In some embodiments, the formulation has a pH of about pH 1 to about pH 5. In some embodiments, the formulation has a pH of about pH 1.5 to about pH 4. In some embodiments, the formulation has a pH of about pH 3 to about pH 4.

In some embodiments, the Bisphosphocin is present in the formulation in an amount from about 1% to about 20% (weight/weight). In some embodiments, the Bisphosphocin is present in the formulation in an amount from about 5% to about 15% (weight/weight). In some embodiments, the Bisphosphocin is present in the formulation in an amount from about 30% to about 50% (weight/weight).

In some embodiments, the fatty alcohol thickening agent is present in the formulation in an amount from about 1% to about 50% (weight/weight). In some embodiments, the fatty alcohol thickening agent is present in the formulation in an amount from about 1% to about 20% (weight/weight). In some embodiments, the fatty alcohol thickening agent is present in the formulation in an amount from about 1% to about 10% (weight/weight).

In some embodiments, the nonionic polymer emulsifier is present in the formulation in an amount from about 0.25% to about 15% (weight/weight). In some embodiments, the nonionic polymer emulsifier is present in the formulation in an amount from about 0.5% to about 5% (weight/weight).

In some embodiments, the formulation further comprises a diluent selected from the group consisting of water, glycerol, mannitol, saline, and phosphate buffered saline. In some embodiments, the diluent is water. In some embodiments, the water is present in the formulation in an amount from about 65% to about 97.5% (weight/weight).

In some embodiments, the fatty alcohol thickening agent is selected from the group consisting of cetyl alcohol, lauryl alcohol, stearyl alcohol, cetosteryl alcohol, myristyl alcohol, docosanol alcohol, and oleyl alcohol. In some embodiments, the fatty alcohol thickening agent is cetosteryl alcohol. In some embodiments, the cetosteryl alcohol is present in the formulation in an amount from about 2% to about 10% (w/w).

In some embodiments, the nonionic polymer is selected from the group consisting of ceteth-20, steareth-20, and ceteareth-20. In some embodiments, the nonionic polymer emulsifier is ceteareth 20. In some embodiments, the ceteareth-20 is present in the formulation in an amount greater than about 0.5% (w/w). In some embodiments, the ceteareth-20 is present in the formulation in an amount of about 0.5% to about 5% (w/w).

In some embodiments, the formulation is adapted for topical administration.

Another aspect of the present disclosure provides a method of treating an infection in a patient in need thereof, the method comprising administering an effective amount of a formulation of the present disclosure to the patient. In some embodiments, the infection is an infection of a diabetic foot ulcer. In some embodiments, the infection is an infection of a burn wound. In some embodiments, the infection is an infection of a complicated venous leg ulcer. In some embodiments, the infection is an otitis externa infection.

Another aspect of the present disclosure provides a method of treating acne vulgaris in a patient in need thereof, the method comprising administering an effective amount of a formulation of the present disclosure to the patient.

Another aspect of the present disclosure provides a method of treating otitis externa in a patient in need thereof, the method comprising administering an effective amount of a formulation of the present disclosure to the patient.

Another aspect of the present disclosure provides a method of treating onychomycosis in a patient in need thereof, the method comprising administering an effective amount of a formulation of the present disclosure to the patient.

Another aspect of the present disclosure provides a method of treating conjunctivitis in a patient in need thereof, the method comprising administering an effective amount of a formulation of the present disclosure to the patient.

In some embodiments, the patient is administered at least one additional active ingredient. In some embodiments, the patient is a human.

Another aspect of the present disclosure provides a formulation of the present disclosure for use in therapy.

Another aspect of the present disclosure provides a formulation of the present disclosure for use in the treatment of an infection.

Another aspect of the present disclosure provides a formulation of the present disclosure for use in the treatment of an infection of a diabetic foot ulcer.

Another aspect of the present disclosure provides a formulation of the present disclosure for use in the treatment of an infection in a burn wound.

Another aspect of the present disclosure provides a formulation of the present disclosure for use in the treatment of an infection of a complicated venous leg ulcer.

Another aspect of the present disclosure provides a formulation of the present disclosure for use in the treatment of acne vulgaris.

Another aspect of the present disclosure provides a formulation of the present disclosure for use in the treatment of otitis externa.

Another aspect of the present disclosure provides a formulation of the present disclosure for use in the treatment of onychomycosis.

Another aspect of the present disclosure provides a formulation of the present disclosure for use in the treatment of conjunctivitis.

Another aspect of the present disclosure provides a formulation of the present disclosure for use in the manufacture of a medicament. In some embodiments, the medicament is for treating an infection in a burn wound. In some embodiments, the medicament is for treating an infection in a diabetic foot ulcer. In some embodiments, the medicament is for treating an infection in a complicated venous leg ulcer. In some embodiments, the medicament is for treating acne vulgaris. In some embodiments, the medicament is for treating otitis externa. In some embodiments, the medicament is for treating onychomycosis. In some embodiments, the medicament is for treating conjunctivitis. In some embodiments, the medicament is adapted for topical administration.

One advantage of a formulation according to an embodiment of the present disclosure is that the mechanism of action of the activity of the Bisphosphocins is effective against many different clinically relevant pathogenic bacteria, including both gram positive and gram negative bacteria. Another advantage of a formulation according to an embodiment of the present disclosure is that such formulation of an embodiment is non-toxic to a patient treated with an effective amount of the formulation of the present disclosure.

A further advantage of a formulation according to an embodiment of the present disclosure is that such formulation is useful for treating infections caused by biofilms. Another advantage of a formulation according to an embodiment of the present disclosure is that the formulation may be administered in an effective amount to treat a patient suffering from a dermatological disorder, an ophthalmic condition, or a wound. Another advantage of a formulation according to an embodiment of the present disclosure is that such formulation can be used during or after surgery (for example, in connection with surgical incisions or implants).

A further advantage of a formulation according to an embodiment of the present disclosure is that such formulation may be administered in an effective amount to treat a patient suffering from a dermatological disorder (such as, for example, complicated skin and skin structure infections (cSSSI), acne vulgaris, otitis externa, or onychomycosis), an ophthalmic condition (such as, for example, conjunctivitis (pink eye), or a wound (for example, burn wounds, complicated diabetic foot ulcers (cDFCU) or complicated venous leg ulcers (cVLU)).

These and other objects, advantages, and features of the present disclosure will become apparent to those skilled in the art upon reading the details of the compounds and formulations according to the present disclosure and uses thereof as more fully described below.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

The present disclosure provides a gel formulation. In some embodiments, the gel formulation includes a Bisphosphocin selected from the group consisting of Nu-2, Nu-3, Nu-4, Nu-5, and Nu-8, or a pharmaceutically acceptable salt thereof, or any combination thereof. As used herein, the term "Bisphosphocin" refers to a class of chemical compounds having antimicrobial activity, including Nu-2, Nu-3, Nu-4, Nu-5, and Nu-8, or a pharmaceutically acceptable salt thereof. U.S. Pat. Nos. 6,627,215, 6,211,162, 7,868,162, 7,176,191, 8,435,960, and 6,211,349, all of which are hereby incorporated by reference in their entireties, disclose Bisphosphocins and how to make and use Bisphosphocins.

As used herein, the term "formulation" refers to a pharmaceutical preparation that contains a Bisphosphocin, or a pharmaceutically acceptable salt thereof, and is suitable for administration to a patient for therapeutic purposes. As used herein, the term "patient" refers to a living organism that is treated with a Bisphosphocin, including without limitation any mammal such as, for example, humans, other primates (e.g., monkeys, chimpanzees, etc.), companion animals (e.g., dogs, cats, horses, etc.), farm animals (e.g., goats, sheep, pigs, cattle, etc.), laboratory animals (e.g., mice, rats, etc.), and wild and zoo animals (e.g., wolves, bears, deer, etc.). As used herein, the term "gel" refers to a semi-solid formulation comprising a polymer network that is able to trap and contain fluids. As used herein, the term "semi-solid" refers to the rheological properties of a formulation, such that the formulation will flow under an applied force but will remain in situ following application to any accessible body surface of a patient.

The chemical name of Nu-2 is ((2R,3R,4R,5R)-5-(2,4-dioxo-3,4-dihydropyrimidin-1(2H)-yl)-3-((hydroxy(4-hydroxybutoxy)phosphoryl)oxy)-4-methoxytetrahydrofuran-2-yl)methyl (4-hydroxybutyl) hydrogen phosphate. The molecular formula of Nu-2 is $C_{18}H_{32}N_2O_{14}P_2$. Nu-2 has the following formula:

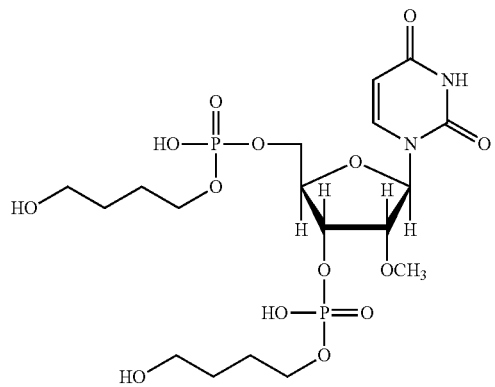

The chemical name of Nu-3 is (2R,3S)-2-((butoxy(hydroxy)phosphoryl)oxy)methyl)-5-(5-methyl-2,4-dioxo-3,4-dihydropyrimidin-1(2H)-yl)tetrahydrofuran-2-yl) butyl hydrogen phosphate. The molecular formula of Nu-3 is $C_{18}H_{32}N_2O_{11}P_2$. Nu-3 has the following formula:

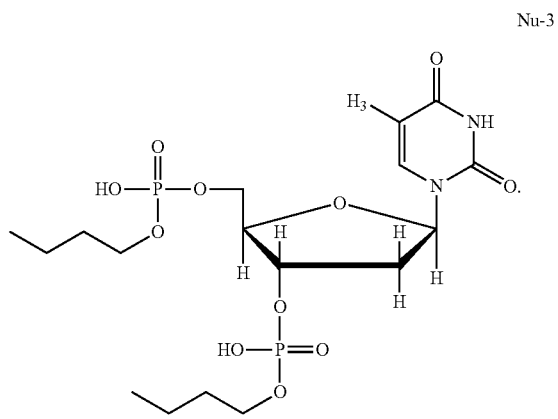

The chemical name of Nu-4 is ((2R,3S)-3((butoxy(hydroxy)phosphoryl)oxy)tetrahydrofuran-2-yl) methyl butyl hydrogen phosphate. The molecular formula of Nu-4 is $C_{13}H_{28}O_9P_2$. Nu-4 has the following formula:

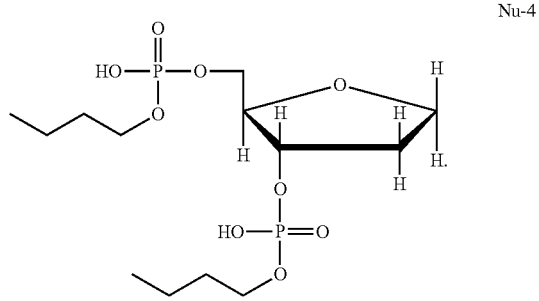

The chemical name of Nu-5 is Dibutyl (oxybis(ethane-2,1-diyl)) bis(hydrogen phosphate). The molecular formula of Nu-5 is $C_{12}H_{28}O_9P_2$. Nu-5 has the following formula:

Nu-5

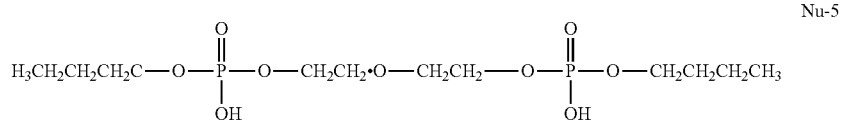

The chemical name of Nu-8 is ((2R,3S,5R)-5-(4-amino-2-oxopyrimidin-1(2H)-yl)-3-((butoxyoxidophosphor-yl)oxy)tetrahydrofuran-2-yl)methyl butyl phosphate. The molecular formula of Nu-8 is $C_{17}H_{29}N_3Na_2O_{10}P_2$. Nu-8 has the following formula:

Nu-8

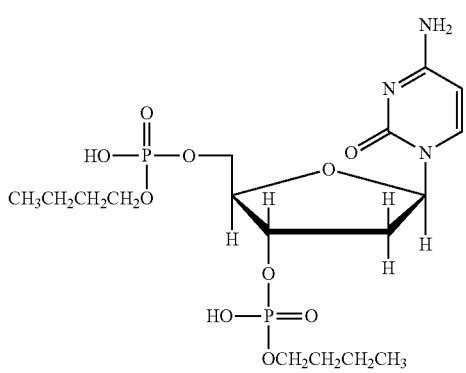

As used herein, the term "pharmaceutically acceptable," with respect to salts and formulation components such as carriers, excipients, and diluents, refers to those salts and components which are not deleterious to a patient and which are compatible with other ingredients, active ingredients, salts or components. Pharmaceutically acceptable includes "veterinarily acceptable," and thus includes both human and non-human mammal applications independently.

As used herein, the term "pharmaceutically acceptable salt" refers to salts commonly used to form alkali metal salts and to form addition salts of free acids or free bases. Such salts include, for example, the physiologically acceptable salts listed in Handbook of Pharmaceutical Salts: Properties, Selection and Use, P. H. Stahl and C. G. Wermuth (Eds.), Wiley-VCH, New York, 2002, which are known to the skilled artisan. Salt formation can occur at one or more positions having labile protons. The pharmaceutically acceptable salts of a Bisphosphocin include both acid addition salts and base addition salts.

A Bisphosphocin is useful as an antimicrobial having activity against any microbe. As used herein, the terms "microbe," "microbial," and like terms refers to bacteria, fungi, protozoa, viruses, yeast, and the like. As used herein, the term "antimicrobial" refers to a Bisphosphocin having the ability to kill or inhibit the growth of a microbe, or to attenuate the severity of a microbial infection.

A non-limiting list of the bacteria that a Bisphosphocin is effective against include without limitation gram positive bacteria, gram negative bacteria, slow growing bacteria and acid fast bacteria, and any species included in the following genera: *Aerococcus, Listeria, Streptomyces, Chlamydia, Lactobacillus, Eubacterium, Burkholderia, Stentrophomo-nas, Achromobacter, Arachnid, Mycobacterium, Peptostreptococcus, Staphylococcus, Corynebacterium, Erysipelothrix, Dermatophilus, Rhodococcus, Pseudomonas, Streptococcus, Bacillus, Peptococcus, Pneumococcus, Micrococcus, Neisseria, Klebsiella, Kurthia, Nocardia, Serratia, Rothia, Escherichia, Propionibacterium, Actinomyces, Helicobacter, Enterococcus, Shigella, Vibrio, Clostridium, Salmonella, Yersinia*, and *Haemophilus*.

Bisphosphocins can be used to treat nosocomial infections. A non-limiting list of specific bacteria that cause nosocomial infections that a Bisphosphocin is effective against include without limitation *Acinetobacter iwoffii* (clinical isolate), *Acinetobacter baumannii* (clinical isolate), *Clostridium difficile* (multi-resistant), *Enterococcus faecalis* (W.T. & vancomycin resistant), *Enterococcus faecium* (vancomycin resistant), *Klebsiella pneumoniae* (clinical isolate and NDM-1), *Pseudomonas aeruginosa* (W.T.), *Pseudomonas aeruginosa* (ciprofloxacin, MDR), *Serratia marcessens* (oxacilllin resistant), *Staphylococcus aureus* (vancomycin), and *Staphylococcus epidermis* (oxacillin resistant).

Bisphosphocins can be used to treat community acquired infections. A non-limiting list of specific bacteria that cause community acquired infections that a Bisphosphocin is effective against include without limitation *Aeromonas hydrophilia* (clinical isolate), *Alcaligenes faecalis* (clinical isolate), *Borellia burgdorferi, Haemophilus influenza, Mycobacterium tuberculosis* (WT, MDR), *Moraxella catarrhalis, Neisseria meningitidis* (rifampicin resistant), *Propionibacterium acnes, Proteus mirabilis*, and *Streptococcus pneumoniae* (penicillin resistant).

Bisphosphocins can be used to treat food borne pathogens. A non-limiting list of specific food borne pathogens that a Bisphosphocin is effective against include without limitation *Esherichia coli* (ampicillin resistant, NDM-1), *Salmonella choleraesuis* (enterica), and *Salmonella typhimurium* (streptomycin resistant).

A non-limiting list of the fungi that a Bisphosphocin is effective against include without limitation *Trichophyton, Epidertnophyion, Microsporum, Candida albicans* and other *Candida* species, *Pityrosporum orbiculare, Trichophyton mentagrophytes, Trichophyton rubrum, Epidermophyton floccosurn*, and *Trichophyton tonsurans*. A non-limiting list of the viruses that a Bisphosphocin is effective against include without limitation human immunodeficiency virus (HIV), herpes simplex virus (HSV), cytomegalovirus (CMV), Hepatitis B virus (HBV), Hepatitis C virus (HCV), and influenza virus. Unless specified to the contrary, specification of a compound of the present disclosure herein includes pharmaceutically acceptable salts of such compounds.

A non-limiting list of specific fungal pathogens that a Bisphosphocin is effective against include without limitation *Trichophylan rubrum* and *memagrophytes, Microsporum gypseum*, and *Aspergillus fumigatus*.

In some embodiments, a Bisphosphocin is useful in both therapeutic and non-therapeutic medical applications. In some embodiments including non-therapeutic medical applications, the antimicrobial effect of a Bisphosphocin allows use of a Bisphosphocin for sterilization (e.g., sterilization of a patient's skin or of a surface or an object, such as, for example, a surgical instrument), or sanitization (e.g., the cleansing of a surface, instrument, as to render the surface free of undesirable concentrations of disease causing microorganisms). In some embodiments, the compounds of the present disclosure are effective in combating microbial contamination of laboratory cultures, consumables (e.g., food or beverage preparations), medical devices, hospital apparatus, or industrial processes. Therapeutic applications of a Bisphosphocin are described herein.

In some embodiments of the present disclosure, the gel formulation includes a fatty alcohol thickening agent. As used herein, the term "fatty alcohol thickening agent" refers to a fatty alcohol compound or composition that increases the viscosity of a formulation of the present disclosure without substantially modifying such formulation's other properties. In some embodiments, the fatty alcohol thickening agent is selected from the group consisting of cetyl alcohol, lauryl alcohol, stearyl alcohol, cetosteryl alcohol, myristyl alcohol, docosanol alcohol, and lauryl alcohol, or combinations thereof. In some embodiments, the fatty alcohol thickening agent is cetosteryl alcohol. In some embodiments, the cetosteryl alcohol is present in the formulation in an amount from about 2% to about 10% (w/w). In some embodiments, cetosteryl alcohol is used such that the end viscosity is from 10 to 50000 centipoise (cps). In some embodiments, the end viscosity is from 500 to 20000 cps.

A particular challenge overcome by the formulations described herein is identifying emulsifiers suitable for a low pH gel formation containing charged molecules such as the Bisphosphocins. Typical ionic polymers, such as polyethylene glycol (PEG) esters, could not be used in the disclosed gel formulations due to the electrostatic interactions with the Bisphosphocins, leading the gel to collapse. Instead, anionic polymers that could withstand low pH are needed.

In some embodiments of the present disclosure, the gel formulation includes a nonionic polymer emulsifier. As used herein, the term "nonionic polymer emulsifier" refers to a nonionic surfactant. In some embodiments, the nonionic polymer is selected from the group consisting of polysorbate 20, polysorbate 60, polysorbate 80, ceteareth-12, ceteareth-20 (or Cetomacrogol 1000), ceteareth 30, ceteth-10, ceteth-20, steareth-10, steareth-20, steareth-40, and steareth-100. In some embodiments, the nonionic polymer emulsifier is selected from the group consisting of ester based products such as PEG-100 stearate, PEG-40 stearate, PEG-120 glyceryl laurate, PEG-40 castor oil, PEG-60 hydrogenated castor oil, PEG-75 lanolin, PEG-120 and methyl glucose dioleate. As used herein, "Cetomacrogol 1000" also means polyethylene glycol hexadecyl ether.

In some embodiments, the nonionic polymer emulsifier is ceteareth 20. In some embodiments, the ceteareth-20 is present in the formulation in an amount greater than about 0.5% (w/w). In some embodiments, the ceteareth-20 is present in the formulation in an amount of about 0.5% to about 5% (w/w).

In some embodiments, the formulation may include other pharmaceutically acceptable components to provide an improved formulation of a Bisphosphocin, including without limitation other pharmaceutically acceptable carriers, excipients or diluents. The other carrier, excipient or diluent may take a wide variety of forms depending on the form of preparation desired for administration.

In some embodiments, the formulation further comprises a diluent selected from the group consisting of water, glycerol, mannitol, saline, and phosphate buffered saline. In some embodiments, the diluent is water. In some embodiments, the water is present in the formulation in an amount from about 65% to about 97.5% (weight/weight).

In some embodiments of the present disclosure, the amount of the Bisphosphocin present in the formulation varies. In some embodiments, the Bisphosphocin is present in the formulation in an amount from about 1% to about 20% (weight/weight). In some embodiments, the Bisphosphocin is present in the formulation in an amount from about 5% to about 15% (weight/weight). In some embodiments, the Bisphosphocin is present in the formulation in an amount from about 30% to about 50% (weight/weight).

In some embodiments of the present disclosure, the amount of the fatty alcohol thickening agent present in the formulation varies. In some embodiments, the fatty alcohol thickening agent is present in the formulation in an amount from about 1% to about 50% (weight/weight). In some embodiments, the fatty alcohol thickening agent is present in the formulation in an amount from about 1% to about 20% (weight/weight). In some embodiments, the fatty alcohol thickening agent is present in the formulation in an amount from about 1% to about 10% (weight/weight). In some embodiments, the fatty alcohol thickening agent is present in the formulation in an amount from about 2% to about 8% (weight/weight).

In some embodiments of the present disclosure, the amount of the nonionic polymer emulsifier present in the formulation varies. In some embodiments, the nonionic polymer emulsifier is present in the formulation in an amount from about 0.25% to about 15% (weight/weight). In some embodiments, the nonionic polymer emulsifier is present in the formulation in an amount from about 0.5% to about 5% (weight/weight).

Because the Bisphosphocins as a class are more active at lower pH, it is necessary to create suitable gel formulations that retain the antimicrobial activity of the Bisphosphocins while maintaining the physical integrity of the gel. It is rare for gels to be formulated at pH levels in the desired pH range of about pH 1 to about pH 5, and even more so at pH 3 or below. The inventors of the present disclosure successfully formulated a unique combination of the active ingredient, thickening agent, and emulsifier to achieve this goal. To achieve the desired pH, in some embodiments, the formulation has a pH of about pH 1 to about pH 5. In some embodiments, the formulation has a pH of about pH 1.5 to about pH 4. In some embodiments, the formulation has a pH of about pH 3 to about pH 4.

The activity of the Bisphosphocins is pH dependent. Therefore, the formulations of some embodiments of the present disclosure also comprise a pH adjusting agent. In some embodiments, the pH adjusting agent can be an acid (such as 10% HCl), an acid salt, or mixtures thereof. Further, the pH adjusting agent can also be a buffer. Suitable buffers include citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers, ammonium/ammonia buffers, and the like. In some embodiments, the pH adjusting agent is present in an amount sufficient to adjust the pH of the composition to about pH 1.0 to about pH 5.0. In some embodiments, the pH adjusting agent is present in an amount sufficient to adjust the pH of the composition to about pH 2 to about pH 4. In another aspect of the disclosure, the pH adjusting agent is present in an amount sufficient to adjust the pH of the composition to about pH 3 to about pH 4.

In some embodiments, the formulations of the present disclosure are adapted for topical administration. As used herein, the term "topical administration" refers to administration of a Bisphosphocin to the skin surface of a patient so that a Bisphosphocin passes through the skin layer. Transdermal administration and transmucosal administration are also encompassed within the term topical administration. As used herein, the term "transdermal" refers to passage of a Bisphosphocin across at least one skin layer of a patient. As used herein, "transmucosal" refers to passage of Bisphosphocin across a mucous membrane of a patient. Unless otherwise stated or implied, the terms "topical administration," "transdermal administration," and "transmucal administration" are used interchangeably herein.

A variety of topical delivery systems for delivering bioactive compounds to microbes in an patient are well known in the art. Such systems include without limitation lotions, creams, gels, oils, ointments, solutions, suspensions, emulsions, and the like by choice of appropriate carriers in the art.

In some embodiments, other materials may also be added to the topical formulations of the present disclosure have additional moisturizing effects and to improve the consistency of the formulation. Examples of such compounds include without limitation cetyl esters wax, stearyl alcohol, cetyl alcohol, glycerin, methyl paraben, propyl paraben, quaternium-15, humectants, volatile methylsiloxane fluids, and polydiorganosiloxane-polyoxyalkylene. If it is desirable for the formulation to have additional cleaning effects in some embodiments, chemicals such as sodium lauryl sulfate or a metal salt of a carboxylic acid may be added.

The present disclosure also provides a method of treating an infection in a patient in need thereof. In some embodiments, the method comprises administering an effective amount of a formulation of the present disclosure to the patient. As used herein, the term "infection" refers to any microbe infection of a patient's body. Infection includes the invasion of a patient's body by a microbe and subsequent multiplication in the patient's body.

As used herein, the terms "treating," "treatment," "therapy," and like terms refer to administration of a Bisphosphocin or formulation of the present disclosure in an amount effective to prevent, alleviate or ameliorate one or more symptoms of a disease or condition (i.e., indication) and/or to prolong the survival of the patient being treated. In some embodiments, "treating," "treatment," "therapy," and like terms also include without limitation reducing or eliminating infection in a patient.

In carrying out the methods of the present disclosure, an effective amount of a Bisphosphocin is administered to a patient in need thereof. As used herein, the term "effective amount," in the context of administration, refers to the amount of a Bisphosphocin of the present disclosure that when administered to a patient is sufficient to prevent, alleviate or ameliorate one or more symptoms of a disease or condition (i.e., indication) and/or to prolong the survival of the patient being treated. Such an amount should result in no or few adverse events in the treated patient. Similarly, such an amount should result in no or few toxic effects in the treated patient. As those familiar with the art will understand, the amount of a Bisphosphocin will vary depending upon a number of factors, including without limitation the activity of a Bisphosphocin (in vitro, e.g. a Bisphosphocin vs. target, or in vivo activity in animal efficacy models), pharmacokinetic results in animal models (e.g., biological half-life or bioavailability), the type of patient being treated, the patient's age, size, weight, and general physical condition, the disorder associated with the patient, and the dosing regimen being employed in the treatment.

In some embodiments, a Bisphosphocin is suitable for administration at a dose of from about 1% to about 15%. In some embodiments, a Bisphosphocin is suitable for administration at a dose of from about 2% to about 10%. In some embodiments, a Bisphosphocin is suitable for administration at a dose of from about 3% to about 8%. In some embodiments, a Bisphosphocin is suitable for administration at a dose of about 5%.

The present disclosure also provides a method of treating an infection of a lower extremity ulcer in a patient in need thereof. In some embodiments, the method comprises administering an effective amount of a Bisphosphocin, or a pharmaceutically acceptable salt thereof, to the patient. As used herein, the term "lower extremity" refers to a lower limb of a patient's body, including without limitation the hip, thigh, leg, ankle, and foot. As used herein, the term "ulcer" refers to an open wound found anywhere on the lower extremity of a patient.

In some embodiments, the patient is a human. In some embodiments, the administration is topical administration. In some embodiments, the administration is carried out using a Bisphosphocin, or a pharmaceutically acceptable salt thereof, in a lotion, paste, cream, ointment, oil or other viscous composition. In some embodiments, the patient is administered at least one additional active ingredient. In some embodiments, the administration is carried out as a multiple dose regimen. As used herein, the term "multiple dose regimen" refers to a treatment time period of more than one day.

In some embodiments, the present disclosure provides a method of treating an infection of a diabetic foot ulcer in a patient in need thereof. In some embodiments, the method comprises administering an effective amount of a Bisphosphocin, or a pharmaceutically acceptable salt thereof, to the patient. In some embodiments, the patient is suffering from Type I diabetes or Type II diabetes. As used herein, the term "diabetic foot ulcer" refers to an open wound located anywhere on the foot of a patient. In some embodiments, the wound is located on the heel, mid-foot, and/or forefoot of the patient's foot. As used herein, the term "treating," in the context of a diabetic foot ulcer, also includes without limitation (a) limiting the progression in size, area, and/or depth of the foot ulcer; (b) reducing size, area, and/or depth of the foot ulcer; (c) increasing rate of healing and/or reducing time to healing; (d) healing of the foot ulcer (100% epithelialization with no drainage); and (c) decreased incidence of amputation or slowing in time to amputation.

In some embodiments, the foot ulcer may be caused by any underlying pathology, including but not limited to neuropathy, trauma, deformity, high plantar pressures, callus formation, edema, and peripheral arterial disease. In some embodiments, the human diabetic foot ulcer is one caused, at least in part, by neuropathy and resulting pressure (weight bearing on the extremity due to lack of feeling in the foot). As is known to those of skill in the art, human diabetic foot ulcers tend to be due to neuropathy and pressure, which differs significantly from, for example, murine acute wounds. In some embodiments, the diabetic foot ulcer comprises one or more calluses.

In some embodiments, the diabetic foot ulcer is a chronic ulcer. As used herein, a "chronic" foot ulcer is one that has been present for at least 7 days with no reduction in size. In some embodiments, the chronic foot ulcer is one that has been present for at least 14 days. In some embodiments, the chronic foot ulcer is one that has been at least 21 or 28 days with no reduction in size. In some embodiments, the chronic foot ulcer has not responded (i.e., no reduction in size, area, and/or depth of the foot ulcer; no healing of the foot ulcer) to any other treatment.

The methods of this disclosure can comprise administering the gel formulations described herein as often as deemed appropriate, i.e., once per day, twice per day, etc. The methods according to the present disclosure may further comprise topical administration of the formulation containing a compound of the present disclosure, or a pharmaceutically acceptable salt thereof, for as long as deemed desirable by an attending physician, for example, until healing of the ulcer. In some embodiments, the gel formulation forms a continuous film covering the entire area of the ulcer, including the margins. In some embodiments, the gel formulation is applied with a thickness of approximately 0.25 to 2 mm. In some embodiments, the gel formulation is applied with a thickness of approximately 0.5 to 1.5 mm. In some embodiments, the topical formulation is applied with a thickness of about 1 mm in thickness.

The gel formulations disclosed herein may be applied in any suitable manner, which may include any wound dressings to seal in the formulation deemed appropriate by the human patient or caregiver. Examples of such dressings include, but are not limited to, semipermeable films, foams, hydrocolloids, and calcium alginate swabs.

The methods of the present disclosure relating to diabetic foot ulcers may further comprise debridement in and around the wound in combination with administration of the compound of the present disclosure and pharmaceutical compositions thereof. Debridement of all necrotic, callus, and fibrous tissue is typically carried for treatment of diabetic foot ulcers. Unhealthy tissue is sharply debrided back to bleeding tissue to allow full visualization of the extent of the ulcer and to detect underlying abscesses or sinuses. Any suitable debridement technique can be used, as determined by an attending physician. The wound can then be thoroughly flushed with sterile saline or a non-cytotoxic cleanser following debridement.

In some embodiments, the patient is a human. In some embodiments, the administration is topical administration. In some embodiments, the administration is carried out using a Bisphosphocin, or a pharmaceutically acceptable salt thereof, in a lotion, paste, cream, ointment, oil or other viscous composition. In some embodiments, the patient is administered at least one additional active ingredient. In some embodiments, the administration is carried out as a multiple dose regimen.

The present disclosure also provides a method of treating an infection in a burn wound in a patient in need thereof. In some embodiments, the method comprises administering an effective amount of a Bisphosphocin, or a pharmaceutically acceptable salt thereof, to the patient. As used herein, the term "burn wound" refers to a burn injury to a patient's body involving damage to a patient's skin and possibly tissues underlying the patient's skin. There are three primary types of burn levels known to one of skill in the art, including without limitation first, second, and third degree burns. In some embodiments, the method of treating an infection in a burn wound contemplated by the present disclosure is used to treat a first, second, and/or third degree burn.

In some embodiments, the patient is a human. In some embodiments, the administration is topical administration. In some embodiments, the administration is carried out using a Bisphosphocin, or a pharmaceutically acceptable salt thereof, in a lotion, paste, cream, ointment, oil or other viscous composition. In some embodiments, the patient is administered at least one additional active ingredient. In some embodiments, the administration is carried out as a multiple dose regimen.

In some embodiments, the present disclosure provides a method of treating an infection of a complicated venous leg ulcer in a patient in need thereof. In some embodiments, the method comprises administering an effective amount of a Bisphosphocin, or a pharmaceutically acceptable salt thereof, to the patient. As used herein, the term "complicated venous leg ulcer" refers to an open wound located anywhere on the leg of a patient and resulting from improper functioning of veins.

In some embodiments, the patient is a human. In some embodiments, the administration is topical administration. In some embodiments, the administration is carried out using a Bisphosphocin, or a pharmaceutically acceptable salt thereof, in a lotion, paste, cream, ointment, oil or other viscous composition. In some embodiments, the patient is administered at least one additional active ingredient. In some embodiments, the administration is carried out as a multiple dose regimen.

The present disclosure also provides a method of treating otitis externa in a patient in need thereof. In some embodiments, the method comprises administering an effective amount of a Bisphosphocin, or a pharmaceutically acceptable salt thereof, to the patient. As used herein, the term "otitis externa" refers to an infection of the external ear canal of a patient.

In some embodiments, the patient is a human. In some embodiments, the administration is topical administration. In some embodiments, the administration is carried out using a Bisphosphocin, or a pharmaceutically acceptable salt thereof, in a lotion, paste, cream, ointment, oil or other viscous composition. In some embodiments, the patient is administered at least one additional active ingredient. In some embodiments, the administration is carried out as a multiple dose regimen.

The present disclosure also provides a method of treating acne vulgaris in a patient in need thereof. In some embodiments, the method comprises administering an effective amount of a Bisphosphocin, or a pharmaceutically acceptable salt thereof, to the patient. As used herein, the term "acne vulgaris" refers to an inflammatory disease of the pilosebaceous glands characterized by an eruption of the skin, often pustular in nature but not suppurative.

In some embodiments, the patient is a human. In some embodiments, the administration is topical administration. In some embodiments, the administration is carried out using a Bisphosphocin, or a pharmaceutically acceptable salt thereof, in a lotion, paste, cream, ointment, oil or other viscous composition. In some embodiments, the patient is administered at least one additional active ingredient. In some embodiments, the administration is carried out as a multiple dose regimen.

The present disclosure also provides a method of treating onychomycosis in a patient in need thereof. In some embodiments, the method comprises administering an effective amount of a Bisphosphocin, or a pharmaceutically acceptable salt thereof, to the patient. As used herein, the term "onychomycosis" refers to a fungal infection of the nail.

In some embodiments, the patient is a human. In some embodiments, the administration is topical administration. In some embodiments, the administration is carried out using a Bisphosphocin, or a pharmaceutically acceptable salt thereof, in a lotion, paste, cream, ointment, oil or other viscous composition. In some embodiments, the patient is administered at least one additional active ingredient. In some embodiments, the administration is carried out as a multiple dose regimen.

The present disclosure also provides a method of treating conjunctivitis in a patient in need thereof. In some embodiments, the method comprises administering an effective amount of a Bisphosphocin, or a pharmaceutically acceptable salt thereof, to the patient. As used herein, the term "conjunctivitis" refers to inflammation or infection of the outer membrane of the eyeball and/or the inner eyelid.

In some embodiments, the patient is a human. In some embodiments, the administration is topical administration. In some embodiments, the administration is carried out using a Bisphosphocin, or a pharmaceutically acceptable salt thereof, in a lotion, paste, cream, ointment, oil or other viscous composition. In some embodiments, the patient is administered at least one additional active ingredient. In some embodiments, the administration is carried out as a multiple dose regimen.

The present disclosure also provides a method of treating oral mucositis in a patient in need thereof. In some embodiments, the method comprises administering an effective amount of a Bisphosphocin, or a pharmaceutically acceptable salt thereof, to the patient. As used herein, the term "oral mucositis" refers to inflammation and ulceration of the mucous membranes lining the mouth.

In some embodiments, the patient is a human. In some embodiments, the administration is topical administration. In some embodiments, the administration is carried out using a Bisphosphocin, or a pharmaceutically acceptable salt thereof, in a lotion, paste, cream, ointment, oil or other viscous composition. In some embodiments, the patient is administered at least one additional active ingredient. In some embodiments, the administration is carried out as a multiple dose regimen.

The present disclosure also provides the use of a Bisphosphocin, or a pharmaceutically acceptable salt thereof, for the manufacture of a medicament. As used herein, the term "medicament" refers to a formulation according to the present disclosure. In some embodiments, the formulation is contained in any manufacture, such as, for example, a package, container, and the like.

In some embodiments, Bisphosphocins that are useful in the formulations according to the present disclosure have the structure of Formula (I), (II), (III), (IV), (V) or (VI):

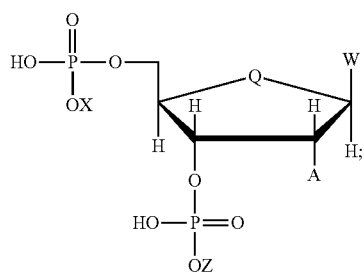
(I)

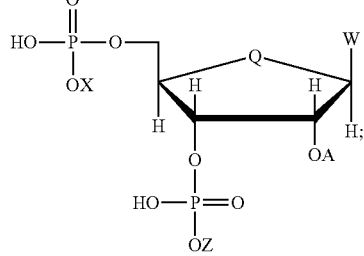
(II)

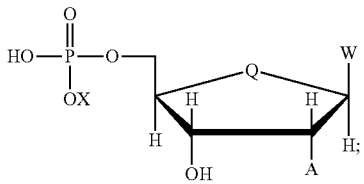
(III)

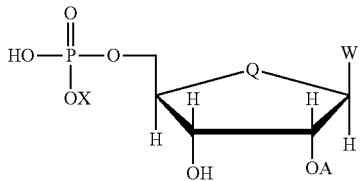
(IV)

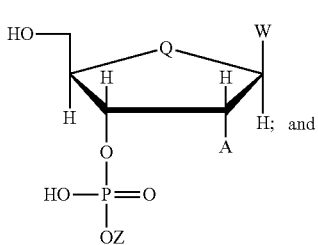
(V)

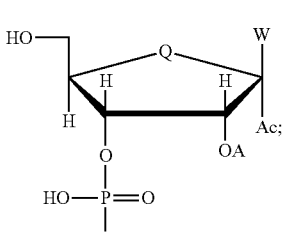
(VI)

wherein A is H, alkyl, alkyl-(O-alkyl), aryl, alkenyl, alkanol, phenol, or enol;

wherein Q is O, S, P—H, P—OH, P-alkyl, P-aryl, P-acyl, N—OH, N-alkyl, N-aryl, N-acyl, —CH$_2$, —CH(OH), or —CH(O-alkyl);

wherein X and Z are alkyl or O-alkyl end blocking groups; and wherein W is H, purine, pyrimidine or a modified analog of a purine or pyrimidine; or a pharmaceutically acceptable salt thereof. In some embodiments, X and/or Z comprises an alkyl end blocking group, and wherein the alkyl moiety is straight chained, branched or cyclic. In some embodiments, the alkyl moiety has one to four carbons and is straight chained. In some embodiments, X and Z have the same chemical moiety. In some embodiments, X and Z have different chemical moieties. In some embodiments, X and Z comprise a butyl group. In some embodiments, X is a butyl group and Z is a butanol. In some embodiments, X is a butanol and Z is a butyl group. In some embodiments, X and/or Z comprises a structure selected from the group consisting of $CH_3CH_2CH_2CH_2—$, $CH_3CH_2CH_2—$, $CH_3CH_2—$, and $HOCH_2CH_2CH_2CH_2—$.

In another embodiment, the compound has the Formula (VII):

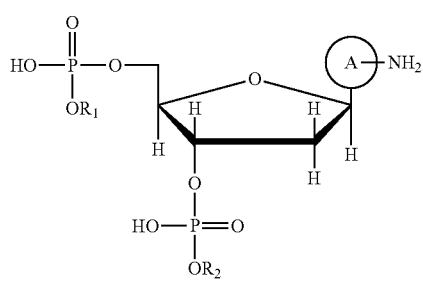

(VII)

wherein Ring A is a stable 5- to 7-membered monocyclic or 7-10-membered bicyclic carbocyclic or heterocyclic moiety that is either saturated or partially unsaturated on which a free amino group is attached to a ring carbon atom, and $R_1$ and $R_2$ are each independently selected from the group of $C_1$-$C_8$ alkyl moieties, which may be branched or unbranched; or a pharmaceutically acceptable salt thereof.

In some embodiments, $R_1$ and $R_2$ are both butyl:

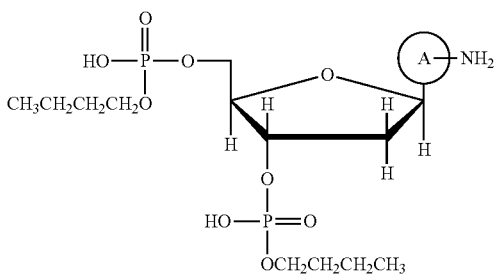

(VIII)

or a pharmaceutically acceptable salt thereof.

In some embodiments of the present disclosure, the Bisphosphocin for use in the formulations of the present disclosure include those having the structure of Formula (IX) shown below:

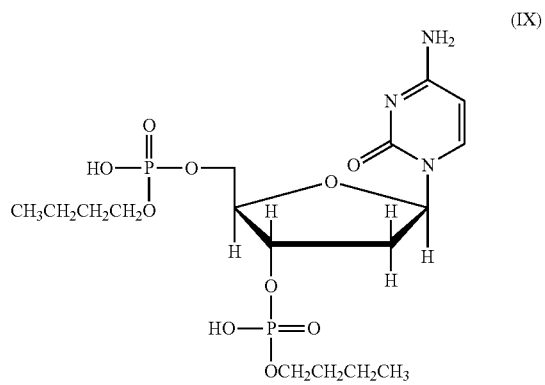

(IX)

or a pharmaceutically acceptable salt thereof.

All pharmaceutically acceptable salt forms of the compounds of Formulas (I)-(IX) are contemplated herein.

Another aspect of the present disclosure provides a method of treating diabetic foot ulcers in a patient in need thereof using the formulations of this disclosure. In some embodiments, the method comprises administering an effective amount of a compound of the present disclosure by applying a formulation according to this disclosure to a patient. In some embodiments, the patient is a human.

Another aspect of the present disclosure provides a method of treating burn wounds in a patient in need thereof using the formulations of this disclosure. In some embodiments, the method comprises administering an effective amount of a compound of the present disclosure by applying a formulation according to this disclosure to the patient. In some embodiments, the patient is a human.

It is another advantage of an embodiment of the present disclosure that the formulation in accordance with some embodiments may be administered in an effective amount to treat a patient suffering from a dermatological disorder (such as, for example, complicated skin and skin structure infections (cSSSI), acne vulgaris, otitis externa, or onychomycosis), an ophthalmic condition (such as, for example, conjunctivitis (pink eye), or a wound (for example, burn wounds, complicated diabetic foot ulcers (cDFCU) or complicated venous leg ulcers (cVLU)). In another embodiment, the gel formulation of this disclosure can be used during or after surgery (for example, in connection with surgical incisions or implants).

The present disclosure also provides a method of treating venous leg ulcers in a patient in need thereof using the formulations of the present disclosure. In some embodiments, the method comprises administering an effective amount of a compound of the present disclosure by applying a formulation according to this disclosure to the patient. In some embodiments, the patient is a human.

The present disclosure also provides a method of treating a dermatological disorder in a patient in need thereof using the formulations of the present disclosure. In some embodiments, the method comprises administering an effective amount of a compound of the present disclosure by applying a formulation according to this disclosure to the patient. In some embodiments, the patient is a human.

The present disclosure also provides a method of treating complicated skin and skin structure infections in a patient in need thereof using the formulations of the present disclosure. In some embodiments, the method comprises administering an effective amount of a compound of the present disclosure by applying a formulation according to this disclosure to the patient. In some embodiments, the patient is a human.

The present disclosure also provides a method of treating acne vulgaris using the formulations of the present disclosure. In some embodiments, the method comprises administering an effective amount of a compound of the present disclosure by applying a formulation according to this disclosure to the patient. In some embodiments, the patient is a human.

The present disclosure also provides a method of treating otitis externa in a patient in need thereof using the formulations of the present disclosure. In some embodiments, the method comprises administering an effective amount of a compound of the present disclosure by applying a formulation according to this disclosure to the patient. In some embodiments, the patient is a human.

The present disclosure also provides a method of treating onychomycosis in a patient in need thereof using the formulations of the present disclosure. In some embodiments, the method comprises administering an effective amount of a compound of the present disclosure by applying a formulation according to this disclosure to the patient. In some embodiments, the patient is a human.

The present disclosure also provides a method of treating an ophthalmic condition in a patient in need thereof using the formulations of the present disclosure. In some embodiments, the method comprises administering an effective amount of a compound of the present disclosure by applying a formulation according to this disclosure to the patient. In some embodiments, the patient is a human.

The present disclosure also provides methods for inhibiting or preventing the growth of bacteria, fungus, or virus, by contacting the infectious organism with a formulation disclosed herein. In some embodiments, the methods are used to treat a mammal. In certain embodiments, the methods are used to treat a human. In some embodiments, the present disclosure provides methods using a formulation of this disclosure to treat a mammal suffering from a bacterial infection caused by *Staphylococcus aureus, Streptococcus pyogenes, Streptococcus pneumoniae, Mycobacterium, Escherichia coli, Aerococcus, Listeria, Streptomyces, Chlamydia, Lactobacillus, Eubacterium, Arachnid, Mycobacterium, Peptostreptococcus, Corynebacterium, Erysipelothrix, Dermatophilus, Rhodococcus, Pseudomonas* (*aeruginosa*), *Streptococcus, Bacillus, Peptococcus, Pneumococcus, Micrococcus, Neisseria, Klebsiella* (*pneumoniae*), *Kurthia, Nocardia, Serratia, Rothia, Escherichia, Propionibacterium, Actinomyces, Helicobacter, Enterococcus* (*Enterococci* spp), *Shigella, Vibrio, Clostridium, Salmonella, Yersinia, Haemophilus Morganella morganii, Proteus mirabilis*, d coagulase-negative *staphylococci*, coagulase negative *Staphylococcus*, Enterobacteriaceae, *E. faecalis*, and *Acinetobacter baumannii*

A range of fungi or molds, called dermatophytes, cause fungal infections of the skin. These fungi are parasites on the skin and cause different symptoms in different pails of the body. They are very infectious and are passed from person to person. Although typically these infections are topical, in certain patients (e.g., immunosuppressed patients) they may occur systemically or internally.

Fungal infections that may be treated with the gel compositions of the present disclosure include dermatophytosis (*Trichophyton, Epidermophyton*, and *Microsporum*), candidiasis (*Candida albicans* and other *Candida* species), tinea versicolor (*Pityrosporum orbiculare*), tinea pedea (*Trichophyton mentagrophytes, Trichophyton rubrum*, and *Epidermophyton floccosurn*), tinea capitis and ringworm (*Trichophyton tonsurans*).

Vaginal yeast infections are generally caused by *Candida albicans*, which, along with a few types of bacteria, are normally present in relatively small numbers in the vaginal area. Sometimes the yeast multiply rapidly and take over, causing candidiasis or monilia. This is often due to a change in the vaginal environment, injury, sexual transmission, HIV infection, etc. Common environmental disruptions that favor yeast include increased pH, increased heat and moisture, allergic reactions, elevated sugar levels, hormonal fluxes, and reductions in the populations of bacteria that are normally present.

In some embodiments, one dosage unit may be administered topically once every 10, 9, 8, 7, 6, 5, 4, 3, 2 days, or 1, 2, 3, 4, 5, 6, 7, 8, 9, 10, or more than 10 times per day until relief is achieved or until the symptoms disappear or are satisfactorily attenuated. In some embodiments, one dosage unit is administered topically about once to about four times per day. In some embodiments, a patient is instructed to take two to three dosage units per day. Treatment regimens using the compositions of the present disclosure can be acute or chronic. In some embodiments, particular dosing regimens include 7, 14, 21 and 28 day dosing.

The present disclosure also provides formulations and therapeutic methods of using a compound of the present disclosure as an active ingredient in a gel formulation containing another active ingredient, e.g., an antibiotic, antifungal, an antiprotozoal, or antiviral. In some embodiments, a compound of the present disclosure is the only active ingredient administered to a patient to treat a microbial infection (such as a bacterial, fungal, viral or protozoan infection), i.e., a compound of the present disclosure is administered as a monotherapy. The monotherapy may be administered with or without a treatment that is not specific to an infection, such as a painkiller (e.g., acetaminophen or a nonsteroidal anti-inflammatory drug such as aspirin, ibuprofen, or naproxen) or numbing agent.

The present disclosure further provides disinfectant compositions comprised of the formulations disclosed herein. The disinfectant composition may be suitable for use on skin, or may be used for disinfection of a surface such as medical devices, e.g. a surgical instrument. The disinfectant composition may also be used in bandages or other dressings to prevent or treat wound infections.

The compounds disclosed for use in the formulations described herein may be present in the form of pharmaceutically acceptable salts. Salt formation can occur at one or more positions having labile protons. The pharmaceutically acceptable salts of the disclosed compounds include both acid addition salts and base addition salts. The term "pharmaceutically acceptable salts" embraces salts commonly used to form alkali metal salts and to form addition salts of free acids or free bases. Such salts include the physiologically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan.

Suitable pharmaceutically acceptable acid addition salts of the disclosed compounds may be prepared from an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, beta-hydroxybutyric, malonic, galactic, and galacturonic acid, to name a few. Pharmaceutically acceptable acidic/anionic salts also include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts, among others.

Suitable pharmaceutically acceptable base addition salts of the disclosed compounds include, but are not limited to, metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine. All of these salts may be prepared by conventional means from the corresponding compound represented by the disclosed compound by treating, for example, the disclosed compounds with the appropriate acid or base. Pharmaceutically acceptable basic/cationic salts also include, the diethanolamine, ammonium, ethanolamine, piperazine and triethanolamine salts, to name a few.

In an embodiment, the pharmaceutically acceptable salt comprises a monovalent cation or a divalent cation. In another embodiment, the pharmaceutically acceptable salt is a bis phosphate diester bis sodium salt.

A compound of the present disclosure may be co-formulated in the gel formulations described herein or co-administered with other active pharmaceutical agents depending on the condition being treated. Co-administration can include simultaneous administration of the two agents in the same dosage form, simultaneous administration in separate dosage forms, and separate administration. In various embodiments, co-administration with respect to a compound of the present disclosure means either at the same time and frequency, or more usually, at different times and frequencies than the compound of the present disclosure, as part of a single treatment plan. Aspects of the present disclosure include the administration of a compound of the present disclosure before, after, and/or during the administration of another antimicrobial agent. An antimicrobial agent (e.g., an agent that generally or specifically targets a microbe) other than a compound of the present disclosure may therefore be used, in combination with a compound of the present disclosure, but yet be administered at different times, different dosages, and at a different frequency, than a compound of the present disclosure.

Doses and Dosing Regimes

The presently described gel formulations comprising a compound of the present disclosure may be formulated with a variety of active ingredients and a variety of physiological carrier molecules. A compound of the present disclosure may optionally be complexed with molecules that enhance their ability to enter the target cells. Examples of such molecules include, but are not limited to, carbohydrates, polyamines, amino acids, peptides, lipids, and molecules vital to bacterial growth.

Administration of the gel formulations of the present disclosure may introduce a compound of the present disclosure to the patient in a diluted amount. In some embodiments, unit dosages suitable for the present disclosure for topical administration may be more than about 1, 5, 10, 50, 100, or 500 mg/kg.

In some embodiments of the present disclosure, the gel formulations contain from about 0.001 percent by weight of a compound of the present disclosure to about 40 percent by weight. In some embodiments, the gel formulations contain from about 0.5% by weight of a compound of the present disclosure to about 30% by weight. In other embodiments, the gel formulations contain from about 1% by weight of a compound of the present disclosure to about 20% by weight. In yet other embodiments, the gel formulations contain from about 5% by weight of a compound of the present disclosure to about 20% by weight.

In one embodiment, one dosage unit may be topically administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is topically administered about once to about four times per day. In some embodiments, dosing regimens for topical administration include 1, 7, 14, 21 and 28 day dosing.

Therapeutic Use of Gel Compositions Containing a Compound of the Present Disclosure The presently described formulations are also contemplated to be effective in combating microbial (e.g., bacterial, fungal, protozoan, or viral) contamination of laboratory cultures, consumables (food or beverage preparations), medical devices, hospital apparatus, or industrial processes.

The gel formulations disclosed herein are particularly useful for treating infections caused by biofilms. Biofilms form when single microorganisms attach to a hydrated surface and grow as an adhesive cell matrix with other microorganisms. The biofilms form densely packed communities of microbial cells which surround themselves with secreted polymers. Biofilms are notoriously difficult to treat and have been implicated in diseases as disparate as atherosclerosis, chronic sinusitis and chronic wound healing.

Bactericidal and/or bacteriostatic activity of the gel formulations including a compound of the present disclosure, or a pharmaceutically acceptable salt thereof, may be measured using any number of methods available to those skilled in the art. One example of such a method is measurement of antibacterial activity through use of a MIC (minimal inhibitory concentration) test that is recognized to be predictive of in vivo efficacy for the topical treatment of a bacterial infection with antibiotics. The gel formulations of the present disclosure display antibacterial activity in this test, even without pretreatment of the bacteria to permeabilize the membrane.

The present disclosure provides methods of inhibiting the growth of microorganisms by contacting the microorganisms with the gel formulations of the present disclosure in which the active agent is a compound of the present disclosure. These methods are effective against infections in vivo, and particularly topical infections. This is demonstrated by test data showing the minimum inhibitory concentrations (MIC) and minimum biocidal concentrations (MBC) of formulations against various pathogenic organisms cultured in vitro under standard conditions. These in vitro tests strongly correlate with in vivo activity, as is evidenced by the widespread use of the MIC and MBC determinations to predict utility of antimicrobial formulations in treatment of infection in animals, including humans.

Particularly striking is the ability of the present gel formulations comprising a compound of the present disclosure to extend the range of antimicrobial effectiveness against bacteria previously considered unreactive towards certain conventional antibiotics. For example, a gel formulation comprising a compound of the present disclosure may be especially useful in formulations to treat acne, diabetic foot ulcers, otitis externa, or burn wounds.

A compound of the present disclosure, as well as having, antibacterial activity, may also have activity as an antifungal. A compound of the present disclosure is thus useful as an active agent in the gel formulation for treatment of fungal infections such as tinea pedea and candidasis.

Gel formulations comprising a compound of the present disclosure may also have activity as an antiviral. Such formulations are thus useful as a topical treatment for viral infections such as herpes simplex.

The gel formulations disclosed herein may also be used as topical disinfectants for sterilization of surfaces such as, for example, countertops, surgical instruments, bandages, or skin; as pharmaceutical formulations, for external application to skin (e.g., as a hand sanitizer) and mucosal surfaces (e.g., a nasal sanitizer), including the cornea, dermal cuts and abrasions, burns, and sites of bacterial or fungal infection; as pharmaceutical formulations, for administration to internal mucosal surfaces such as the oral cavity or vagina to inhibit the growth of bacteria, viruses or fungi, including yeasts; and as pharmaceutical formulations for coating indwelling catheters and similar implants which are susceptible to harboring bacterial or fungal infection.

Antibiotics

The gel formulations of this disclosure may be useful as topical antibiotic formulations including other antibiotic agents, with both prescription agents (e.g., benzomycin) and over-the-counter agents (e.g., salicylic acid, benzoyl peroxide and the like.). When used in the therapeutic treatment of disease, an appropriate dosage of a gel formulation containing a compound of the present disclosure and another active ingredient may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Additionally, therapeutic dosages may also be altered depending upon factors such as the severity of infection, and the size or species of the host.

Antivirals

Because some of the compounds of the present disclosure are based on the natural structures of nucleosides, formulations comprising compounds of the present disclosure may possess efficient antiviral activity.

Viruses that may be treated by the formulations of the present disclosure include, but are not limited to, human immunodeficiency virus (HIV), herpes simplex virus (HSV), cytomegalovirus (CMV), Hepatitis B virus (HBV), Hepatitis C virus (HCV) and influenza virus.

Conjunctive Therapies

The gel formulations comprising a compound of the present disclosure can also be used in conjunction with conventional antimicrobial agents. The added activity of the active ingredients may provide for a more efficacious formulation, and can provide multiple mechanisms by which the microbes are targeted. Pharmaceutical compositions containing a compound of the present disclosure in admixture with another active agent can be prepared according to conventional pharmaceutical compounding techniques.

For example, compositions for the treatment of acne may comprise a compound of the present disclosure with salicylic acid, benzoyl peroxide, and/or sulfur. Such conjunctive therapy using a compound of the present disclosure with another active agent can increase the efficacy of gel formulations of this disclosure without having to increase the amounts of the agents currently available to consumers, e.g., the amount found in over-the-counter products.

Over the counter (OTC) antifungal medications that may be additional active ingredients in the gel compositions of the present disclosure include, but are not limited to: Miconazole, Miconazole nitrate, Polynoxylin, Clotrimazole, Sulconazole nitrate, Econazole nitrate, Tolnaftate, Selenium sulphide, Tioconazole Prescriptive antifungals include drugs such as allylamines, azoles, polyene macrolides, flucytosine, pseudomycins and griseofulvin. Exemplary antifungals include Amphotericin B, Fluconazole/Difluian, Flucytosine, Foscarnet, Itraconazole/Sporonex, Ketoconazble/Nitoral, and Nystatin 1. See also Elewski, *Cutaneous Fungal Infections*, 2nd Edition (1998) and Segal, *Pathogenic Yeasts and Yeast Infections* (1994), which are both incorporated by reference.

The gel formulations of the present disclosure contain a compound of the present disclosure as an active ingredient, and may also contain any of a number of additives that are themselves active ingredients, such as a retinoic acid, glycolic acid, lactic acid, α-hydroxy acids, keto-hydroxy acids, citric acid, glucuronic acid, galacturonic acid, glucuronolactone, gluconolactone, a-hydroxy-butyric acid, α-hydroxyisobutyric acid, malic acid, pyruvic acid, phenyllactic acid, phenylpyruvic acid, saccharic acid, mandelic acid, tartaric acid, tarlronic acid, hydroxybutyric acid, vitamin A palmitate (retinyl pal mitate) and/or vitamin E acetate (tocopheryl acetate). In some embodiments, each of these are present in an amount from about 0.5 wt % to about 20 wt %. In addition, a UV absorbing or blocking material, such as 4-aminobenzoic acid (PABA), may be used.

Additional active ingredients that may be used in the gel formulations of this disclosure include those found in U.S. Pat. No. 5,652,266, directed to combination of α-hydroxy acid, retinoid and salicylic acid; U.S. Pat. No. 5,843,998, directed to a composition containing α-hydroxy acids and carbamide peroxide, either with or without salicylic acid; U.S. Pat. No. 5,153,230, which is directed to a formulation in which the major active ingredient is glycolic acid; U.S. Pat. No. 4,464,392, which is directed to a antimicrobial formulations containing glycolic acid derivatives; and U.S. Pat. No. 4,105,782, which describes numerous other similar active agents that may be used in a gel composition of the present disclosure.

The gel formulations of the present disclosure may also be used as a carrier material for and/or in combination with other medicines, such as spermicidal agents, anti-viral agents and anti-fungal agents, thereby further broadening the compositions medical efficacy. The gel formulations of the present disclosure may also include a topical anesthetic such as lidocaine hydrochloride and topical steroids, such as corticosteroid, to provide relief from pain or itching during treatment.

Use of Gel Formulations as Disinfectants

The gel formulations described herein containing compounds of the present disclosure may also find use as a disinfectant, and as preparations having biostatic or biocidal properties. The disinfectant gel formulations of the present disclosure may also contain other active ingredients with biostatic and/or biocidal properties. For example, the disinfectant gel may contain a compound of the present disclosure with a suitable concentration of a quaternary ammonium compound such as: dimethylbenzyldodecylammonium chloride, dimethylbenzyl decylammonium chloride, dimethylbenzyl decylammonium bromide, and dimethylbenzylloctylammonium chloride.

In another example, suitable microbiocidal biguanidine compounds, such as oligohexamethylene biguanide salts and bisbiguanides, can be used. See, e.g., U.S. Pat. No. 5,030,659. Additional biocidal ingredients include aldehydes, phenol derivatives, and halogen phenyl derivatives. See, e.g., U.S. Pat. No. 5,767,054. Other compounds with such activity, as will be recognized by those skilled in the art, may also be used in conjunction with compounds of the present disclosure in the gel formulations described herein.

These preparations are especially suitable for surface disinfection in medically-related environments, such as hospitals, veterinary clinics, dental and medical offices, and the like. In some embodiments, formulations of the present disclosure are used in the sterilization of surgical instruments. These preparations are also useful in public areas such as schools, public transport, restaurants, hotels and laundries. The disinfectants also find use in home as sanitizers for toilets, basins, and kitchen areas.

EXAMPLES

Examples related to the present disclosure are described below. In most cases, alternative techniques can be used. The examples are intended to be illustrative and are not limiting or restrictive of the scope of the invention as set forth in the claims.

The compounds of the present disclosure are synthesized according to methods known to those of ordinary skill in the art. The methods described in U.S. Pat. Nos. 6,627,215, 6,211,162, 7,868,162, 7,176,191, 8,435,960, and 6,211,349, all of which are hereby incorporated by reference in their entireties, are suited for synthesizing the compounds of the present disclosure. Nu-8 is synthesized according to the following method:

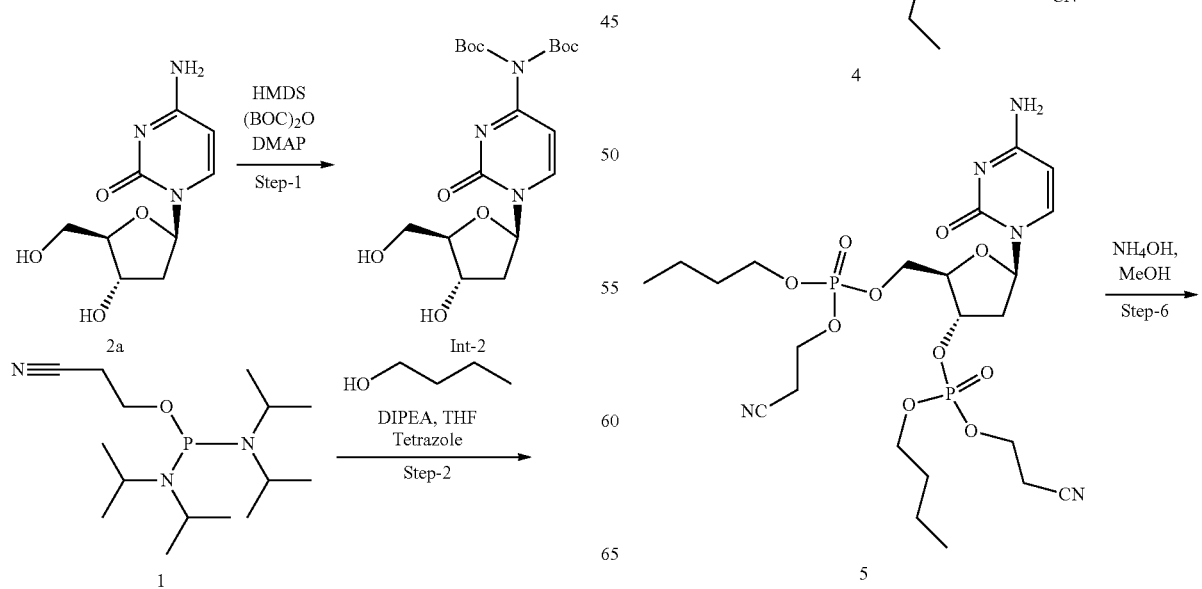

-continued

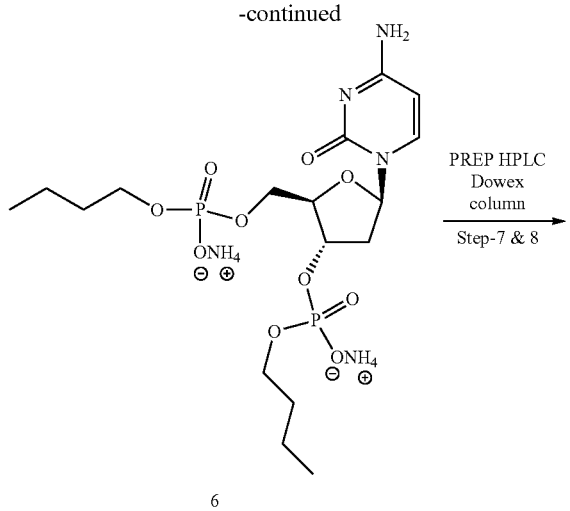

6

Nu-8

Step-1. Cytidine 2a is added to hexamethyldisilazane (HMDS), dimethylamino pyridine (DMAP) and di-tert-butyl dicarbonate ((BOC)$_2$O) to protect the nitrogen atoms of 2a by generating BOC-protected compound Int-2.

Step-2: n-Butanol is reacted with the phosphinamide 1 in THF with tetrazole as a catalyst in the presence of di-isopoylethylamine (DIPEA). The crude product is chromatographed on neutral alumina eluting with hexane and then 2% ethyl acetate in hexane. The pure fractions is combined (by TLC) and evaporated to a residue under vacuo.

Step-3. BOC-protected species Int-2 is bis-phosphinylated with reagent 2 in dichloromethane (DCM)/dimethyl formamide (DMF) solvent and tetrazole as catalyst to produce 3. The reaction mixture is concentrated to a residue and the crude product is immediately oxidized in the next step.

Step-4 & 5: The crude product 3 is oxidized with t-butylhydroperoxide (TBTH) in the presence of decane to generate the bis-phosphonate species 4. Removal of the BOC groups is carried in DCM in the presence of trifluoro acetic acid (TFA) to yield 5. The crude product is chromatographed on silica gel eluting with ethyl acetate. The pure fractions (by TLC) are combined and evaporated to a residue under vacuo.

Step-6: Hydrolysis of 5 with methanolic ammonium hydroxide (NH$_4$OH, MeOH) gives crude (I) ammonium salt (6).

Step-7 & 8: Purification by preparative HPLC of 6 and conversion to the free acid with Dowex 50WX8-200 resin is carried out. Evaporation of the aqueous eluate provides (I) that is diluted with purified water to provide a 20% solution at its ambient pH.

The sodium salt of the compound having the Formula (IX), or Nu-8, is synthesized according to the following method:

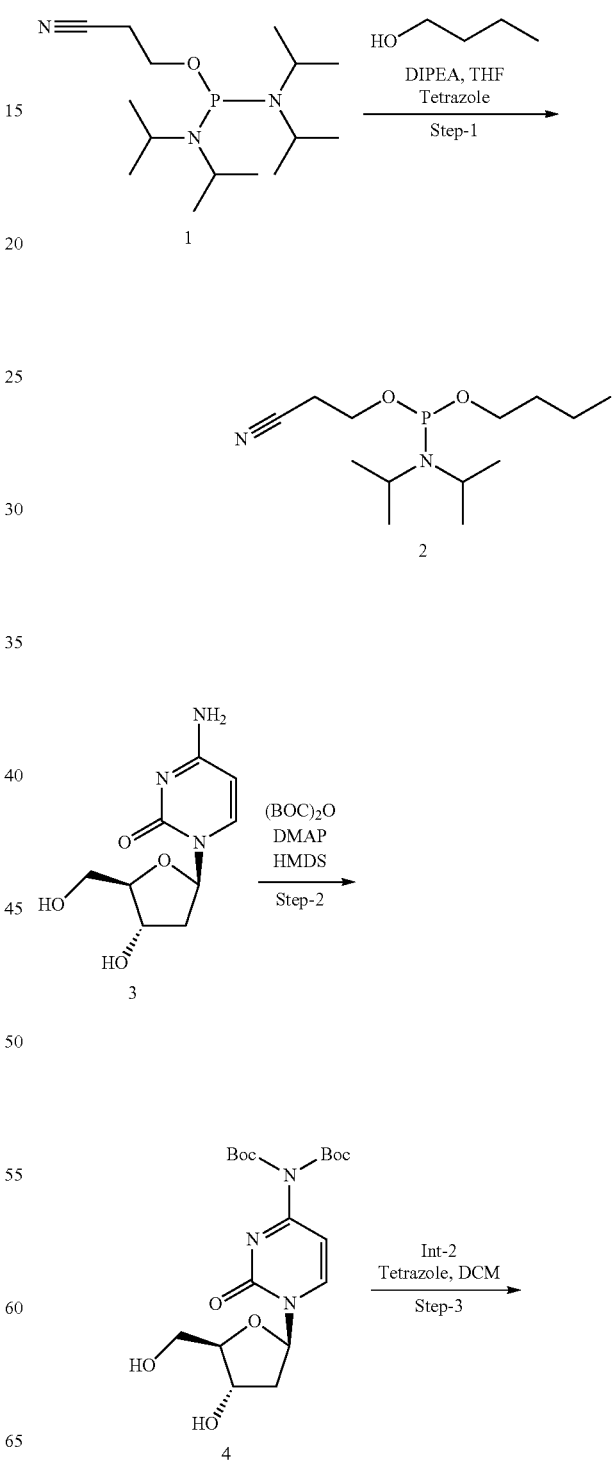

-continued

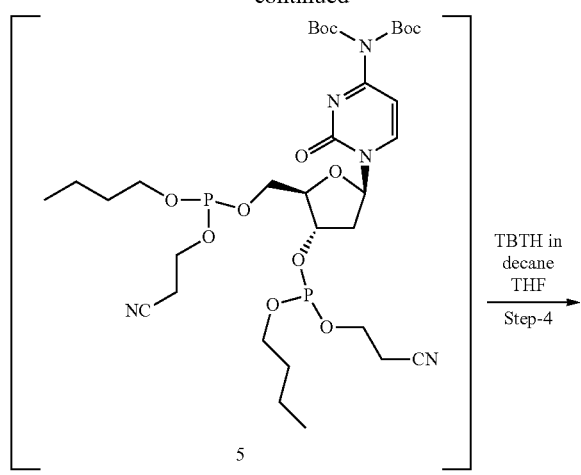

5

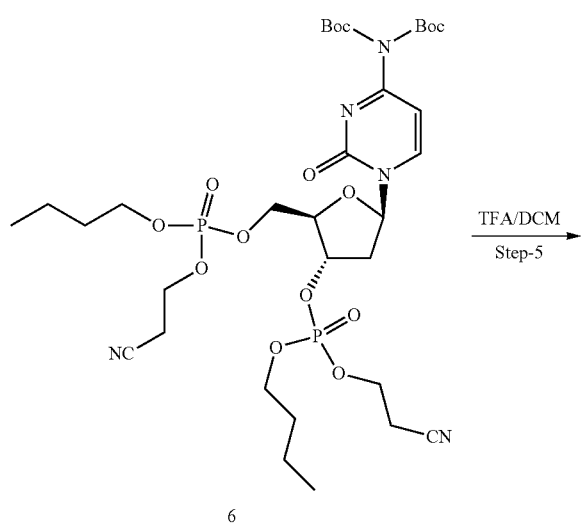

6

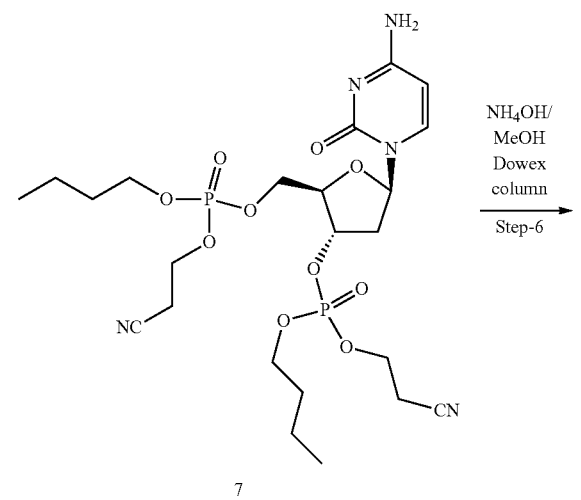

7

-continued

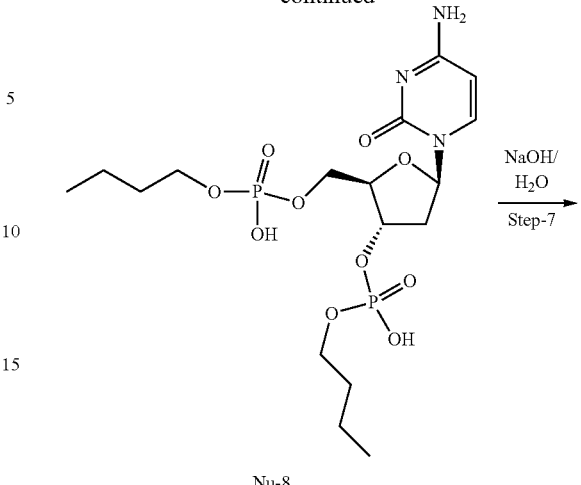

Nu-8

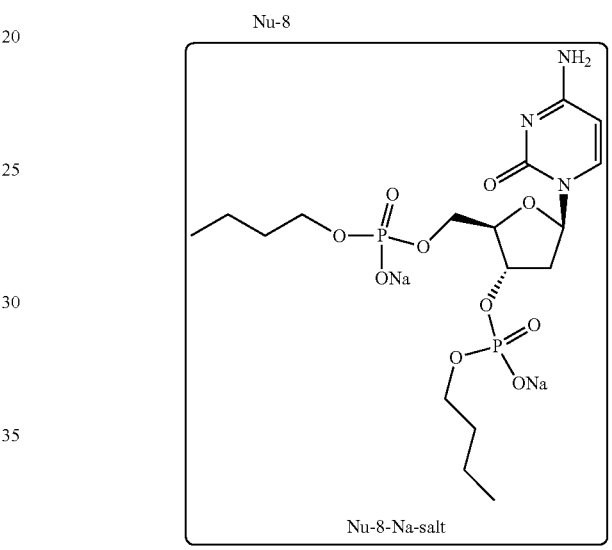

Nu-8-Na-salt

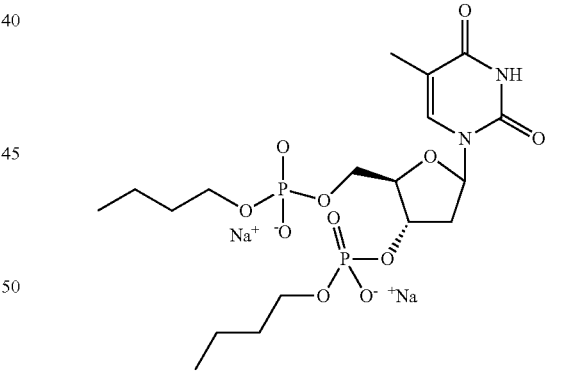

Synthesis of Compound-2: To a solution of compound-1 (1.0 kg, 3.3222 mol) in THF (6 L) is added DIPEA (1.370 ml, 8.3055 mol) and Tetrazole (230 g, 3.3222 mol) followed by n-Butanol (275 ml, 2.99 mol) in THF (6 L) is added drop wise at 0° C. for 12 h. The reaction mixture is stirred at room temperature for 24 h. The progress of the reaction is monitored by TLC and after completion of the reaction, solid is filtered off. Filtrate is evaporated under reduced pressure at 40° C. to afford crude compound. Crude compound is dissolved in ethyl acetate (5 L). Organic layer is washed with water (3 L) and brine (2 L). Organic layer is dried over anhydrous $Na_2SO_4$ filtered and the solvent is evaporated under reduced pressure to get afford crude Compound. The Crude compound is purified by column Chromatography over Basic Alumina ($Al_2O_3$), Compound eluted with 0-2% EtOAc in pet ether to afford compound-2. (700 g, 76.92%) as pale yellow liquid. H-NMR (400 MHz, Chloroform-d) δ 4.18-4.07 (m, 1H), 4.02 (q, J=6.6 Hz, 1H), 3.93-3.74 (m, 4H), 2.65 (td, J=6.5, 3.6 Hz, 2H), 1.31-1.23 (m, 4H), 1.18 (dd, J=6.8, 3.8 Hz, 12H), 0.93 (td, J. 7.4, 3.1 Hz, 3H). LC-MS: 275 (M+H).

Synthesis of Compound-4: To solution of compound-3 (300 g, 1.321 mol) in Hexamethyldisilazane (638 g, 3.964 mol) is added DMAP (16.11 g, 0.132 mol) followed by TMSOTf (7.22 g, 0.039 mol) is added at 0° C. and the resulting reaction mixture is stirred for 1 h at room temperature. After complete of starting material Boc-anhydride (1.4 L, 6.605 mol) is added at 0° C. for 1 h and the reaction mixture is stirred for 16 h at room temperature. To the reaction is added methanol (3 L) followed by triethylamine (1.5 L) is added at 0° C. for 1 h and the reaction mixture is stirred for 20 h at room temperature. Reaction mixture is concentrated under reduced pressure to get crude compound. Crude compound is diluted with ethyl acetate (3 L) and washed with water (1.0 L) and brine (1.0 L) solution; Organic layer is dried over anhydrous $Na_2SO_4$, filtered and the solvent is evaporated under reduced pressure to get afford crude compound. The Crude compound is purified by column Chromatography silica gel (100-200 mesh) Compound eluted 0-3% MeOH in DCM to afford compound-4 (180 g, 31.89%) as off white solid. H-NMR (300 MHz, DMSO-d6) δ 8.41 (d, J=7.5 Hz, 1H), 6.84 (d, J=7.5 Hz, 1H), 6.06 (t, J=6.2 Hz, 1H), 5.28 (d, J=4.3 Hz, 1H), 5.07 (q, J=4.6, 4.0 Hz, 1H), 4.21 (q, J=4.1 Hz, 1H), 3.87 (q, J=3.7 Hz, 1H), 3.71-3.49 (m, 2H), 2.32 (m, 1H), 2.03 (dt, J=13.0, 6.2 Hz, 1H), 1.49 (s, 18H). LC-MS: 275 (M+H).

Synthesis of Compound-6: To a stirred solution of compound-4 (180 g, 0.421 mol) in THF (1.0 L) is added DIPEA (348 mL, 2.105 mol) and Tetrazole (176 g, 2.526 mol) at 0° C. To the resulting reaction mixture is added a solution of compound-2 (519 g, 1.896 mol) in THF (800 ml) drop wise at 0° C. for 1 h. The reaction mixture is stirred at room temperature for 16 h. After completion of the reaction, tort-butyl peroxide in decane (505 ml, 5M) is added drop wise at 0° C. and the reaction mixture is stirred for 6 h at room temperature. The reaction is monitored by TLC. After completion of the reaction, the reaction mixture is concentrated at 40° C. and diluted with ethyl acetate (3 Lit) and washed with water (1 Lit) and brine (1 Lit) solution; Organic layer is dried over anhydrous $Na_2SO_4$ filtered and the solvent is evaporated under reduced pressure to get afford crude compound (350 g, crude). The Crude compound is purified by column chromatography through silica gel (100-200 mesh) column eluted with 0-5% MeOH in DCM. All collected pure fractions are concentrated to afford pure compound-6 (220 g, 64.83%) as a wine red liquid. H-NMR (300 MHz, DMSO-$d_6$) δ 8.19 (dd, J=7.6, 1.3 Hz, 1H), 6.88 (d, J=7.5 Hz, 1H), 6.13 (t, J=10.5 Hz, 1H), 4.99 (s, 1H), 4.44 (s, 1H), 4.26-3.96 (m, 10H), 3.00-2.84 (m, 4H), 2.57-2.79 (m, 2H), 1.70-1.54 (m, 4H), 1.50 (s, 18H). 1.35 (m, 4H), 0.88 (qd, J=7.5, 2.5 Hz, 6H); LC-MS: 806 (M+H).

Synthesis of Compound-7: To a solution of compound-6 (220 g, 0.273 mol) in DCM (4.4 L) is added TFA (210 mL, 2.732 mol) drop wise at 0° C. The reaction mixture is stirred at room temperature for 24 h. The reaction is monitored by TLC. After completion of the reaction, solvent is evaporated under reduced pressure to afford Crude compound. The Crude compound is purified by column Chromatography silica gel (230-400 mesh) Compound eluted with 0-10% MeOH in DCM. All collected pure fractions are concentrated to afford pure compound-7 (170 g, 84.67%) as a pale yellow liquid. H-NMR (300 MHz, DMSO-$d_6$) δ 7.61 (d, J=7.5 Hz, 1H). 7.27 (d, J=13.9 Hz, 2H), 6.19 (t, J=6.9 Hz, 1H), 5.74 (d, J=7.4 Hz, 1H), 4.96 (s, 1H), 4.10-3.93 (m, 11H), 2.93 (q, J=6.2 Hz, 4H), 2.29 (d, J=13.1 Hz, 2H), 1.61 (h, J=7.1 Hz, 4H), 1.35 (p, J=7.3 Hz, 4H), 0.89 (dq, J=7.9, 4.2 Hz, 6H); LC-MS: 606 (M+H).

Synthesis of Nu-8: To a stirred solution of compound-7 (720 g, 1.1900 mol) in MeOH (5.0 L) is added aq. ammonia (600 mL) at 0° C. The reaction mixture is stirred at room temperature for 4 h. The reaction is monitored by TLC. After completion of the reaction, evaporate the MeOH under reduced pressure the aqueous layer is washed with DCM (1.5 L). The aqueous layer is passed through Dowex-$H^+$ resin. The water is removed under reduced pressure to afford Nu-8 (260 g, 43.84%) as an off white solid. H-NMR (300 MHz, DMSO-$d_6$) δ 8.94 (s, 1H), 8.49 (s, 1H), 7.97 (d, J=7.8 Hz, 1H), 6.08 (1, J=6.1 Hz, 1H), 5.95 (d, J=7.7 Hz, 1H), 4.76 (q, J=5.8 Hz, 1H), 4.15 (q, J=4.1 Hz, 1H), 4.08 (s, 1H), 3.83 (m, 6H), 2.43 (t, J=5.6 Hz, 2H), 1.67-1.44 (m, 4H), 1.44-1.26 (m, 4H), 0.95-0.82 (m, 6H). LC-MS: 500.15 (M+H).

Synthesis of Nu-8 Sodium salt: To a stirred solution of compound-Nu-8 (260 g, 0.478 mol) in water (2.6 L), 1N NaOH (950 mL) is added drop wise at 0° C. The reaction mixture is stirred at room temperature for 2 h. The reaction is monitored by TLC. After completion of the reaction, aqueous layer is washed with DCM (1.5 L). The aqueous layer is evaporated under reduced pressure to afford Nu-8 Sodium salt (265 g, 93%) as off white solid. H-NMR (300 MHz, DMSO-$d_6$) δ 7.81 (d, J=7.2 Hz, 1H), 7.2 (bs, 1H), 7.0 (bs, 1H), 6.16 (t, J=4 Hz, 1H), 5.71 (d, J=7.6 Hz, 1H), 4.69 (bs, 1H), 3.75 (m, 1H), 3.71 (m, 1H), 3.8 (m, 4H), 2.2 (q, 1H), 1.89-1.96-1.44 (m, 1H), 1.49-1.39 (m, 4H), 1.34-1.23 (m, 4H), 0.88-0.84 (m, 6H).

All excipients referred to in the following Examples are compendial grade. All solvents for analysis are HPLC grade.

HPLC analysis of Nu-3 is performed using HPLC. The HPLC instrument is an Agilent 1200 system with a diode array detector. Approximately 0.2 g of a Nu-3 fatty alcohol-based gel is added to a 50 mL volumetric flask. For a Nu-3 cellulose-based gel, ~25 mL of water is added, the flask is vortexed to dissolve the gel, then the flask is brought to volume with water. For the fatty alcohol (FA) gel, ~25 mL of warm water (45-50☐) is added with a small stir bar, the flask is mixed for 15 minutes to uniformly disperse the FA gel, the stir bar is removed and the flask is brought to volume with water. The cellulose gel extract is suitable for direct injection; an aliquot of the FA gel extract is centrifuged for 2 minutes to remove undissolved solids.

An Orion 710 A+ meter and electrode (Themo) are used to measure pH. Viscosity is measured with a Brookfield viscometer. Moderate shear mixing for gels are provided by an IKA Eurostar 200 overhead drive with a 1.0" marine propeller. High shear mixing for FA gels is provided by a Omni homogenizer with a 7 mm rotor-stator head at ~10,000 rpm.

Example 1: Cellulose Gel Compounding

The following steps are used to prepare cellulose gels using a solution of Nu-3 as the free acid at the 100 g scale.
1. Add Nu-3 to a portion of the water and mix until homogeneous.
2. Add sodium chloride and mix until homogeneous.
3. Adjust pH to 1.5 (1.4-1.6 acceptable range) using 4% NaOH.
4. Add remaining water and mix until homogeneous.

5. Slowly add hydroxyethyl cellulose powder (Natrosol 250 HHX PH, Ashland) to the vortex of the mixing propeller.

6. Continue mixing until the polymer gel is transparent (~45-60 minutes).

Example 2: Fatty Alcohol (FA) Gel Compounding

The following steps are used to prepare FA gels using a solution of Nu-3 as the disodium salt at the 100 g scale.

1. Add Nu-3 to a portion of the water and mix until homogeneous.
2. Adjust pH to 1.5 (1.4-1.6 acceptable range) using 10% HCl.
3. Add remaining water and mix until homogeneous.
4. In a separate vessel combine cetostearyl alcohol (Crodacol CS 50 NF, Croda) and ceteareth-20 (Cetomacrogol 1000 NE Croda) and heat to ~60° C. on a hot plate with mixing to melt the fatty alcohol and surfactant. Hold at ~60° C.
5. Heat API solution to ~60° C. on a hot plate while mixing with the propeller mixer.
6. Add fatty alcohol/surfactant mixture to the API solution while mixing with the propeller mixer. Remove propeller mixer, remove vessel from heat, and start high shear mixing.
7. Continue high shear mixing as the gel cools and thickens (~45-50° C.).
8. When the gel becomes too thick for mixing with the homogenizer, stop high shear mixing and continue mixing with the propeller mixer until the gel reaches 35-40° C.).

Example 3: Set-Up HPLC Assay and Autoclaving Study

The chromatography conditions in Table 1 are used to assay Nu-3 formulations for this Example.

TABLE 1

| Chromatography conditions. | |
|---|---|
| Column | Phenomenex Kinetex XB-C18 4.6 × 250 mm, 3.5 μm |
| Guard column | Phenomenx SecurityGuard cartridge, C18 (ODS) 4 mm L × 3 mm ID |
| Mobile Phase A | 10 mM ammonium acetate |
| Mobile Phase B | Acetonitrile |
| Gradient | 0.0 min. 95% A |
| | 20.0 min. 5% A |
| | 25.0 min. 5% A |
| | 25.1 min. 95% A |
| | 30.0 min. 95% A |
| Run Time | 30 min. |
| Flow Rate | 1.0 mL/min. |
| UV Detector | 265 nm |
| Injection Volume | 10 μL |
| Column Temperature | 30° C. |

Linearity is evaluated using Nu-3 solutions from 0.05 to 0.4 mg/mL. The correlation coefficient for peak area versus mg/mL has a value of 0.9994. The % Relative Standard Deviation (RSD) for repeated injections of a 0.2 mg/mL standard is <1.0%.

Example 4: Vehicle Gels for Evaluation

Three vehicle gels are prepared for evaluation. Sodium phosphate is used to simulate the presence of the compound of Formula (I) and benzyl alcohol is used as an antimicrobial preservative. Their compositions are summarized in Table 2.

TABLE 2

| Vehicle gel compositions. All numbers are % w/w. | | | |
|---|---|---|---|
| Ingredient | Gel 1 | Gel 2 | Gel 3 |
| Sodium phosphate monobasic (monohydrate), USP | 0.4 | 0.4 | 0.4 |
| 3.5% HCl (q.s. to pH 2.5) | 0.9 | 0.9 | 0.9 |
| Sodium chloride, USP | 0.32 | 0.32 | 0.32 |
| Benzyl alcohol, NF | 0.5 | 0.5 | 0.5 |
| Natrosol HXX1250 NF | 1.00 | 1.75 | 0.0 |
| Crodacol CS 50 NF | 0.0 | 0.0 | 4.0 |
| Cetomacrogol 1000 NF | 0.0 | 0.0 | 1.0 |
| Purified water. USP | q.s. to 100% | q.s. to 100% | q.s. to 100% |

Gels 2 and 3 are selected for formulation with Nu-3 at 5% w/w due to their superior physical properties. The formulation pH is reduced to a target value of 1.5 to ensure optimal activity of Nu-3.

Example 5: 5% NU-3 Cellulose Gel: Formulation and Stability

The composition for this gel is shown in Table 3.

TABLE 3

| 5% cellulose gel composition. All numbers are % w/w. | |
|---|---|
| Ingredient | 5% Nu-3 cellulose gel |
| Nu-3 20% solution | 25.0 |
| 4% NaOH (q.s. to pH 1.5) | 3.0 |
| Sodium chloride, USP | 0.32 |
| Natrosol HXX250 NF | 1.75 |
| Purified water, USP | q.s. to 100% |

The results for initial and stability results for the 5% Nu-3 cellulose gel are summarized in Table 4.

TABLE 4

| Initial and stability results for the 5% Nu-3 cellulose gel. | | | | |
|---|---|---|---|---|
| Time point/ storage condition | Assay, % w/w | Viscosity, cP[1] | Appearance | pH |
| Initial | 4.94 | 12,200 | Viscous gel | 1.43 |
| 1 month, 40° C. | 4.90 | 125 | Liquid | 1.51 |
| 1 month, 30° C. | Not tested | 4,600 | Liquid | Not tested |
| 1 month, 25° C. | Not tested | 6,870 | Slightly viscous liquid | Not tested |
| 1 month, 5° C. | Not tested | 11,200 | Viscous gel | Not tested |

[1]RV viscometer, S14 spindle, 6R small sample adaptor, 30 rpm.

On storage, the cellulose Nu-3 gel's viscosity decreases significantly with temperature. This is likely clue to hydrolysis of the cellulose in the polymer. However, the assay and pH after 1 month of storage at 40° C. has no significant change.

Example 6: 5% NU-3 FA Gel: Formulation and Stability

The composition for these gels are shown in Table 5.

TABLE 5

5% FA gel compositions.

| Ingredient | Nu-3 FA Gel 1 | Nu-3 FA Gel 2 |
|---|---|---|
| Nu-3 disodium salt | 5.36 | 5.36 |
| 10% HCl (q.s. to pH 1.5) | 2.8 | 2.8 |
| Crodacol CS 50 NF | 4.0 | 7.25 |
| Cetomacrogol 1000 NF | 1.0 | 1.0 |
| Purified water, USP | q.s. to 100% | q.s. to 100% |

During compounding, FA Gel 1 fails to thicken.

For FA Gel 2, the cetostearyl alcohol level is increased from 4.0 to 7.25% w/w. This increases the gel viscosity for the vehicle and the 5% Nu-3 formulations. The stability data for Nu-3 FA Gel 2 are summarized in Table 6.

TABLE 6

Initial and stability results for the 5% Nu-3 FA Gel 2.

| Time point/ storage condition | Assay, % w/w | Viscosity, cP[1] | Appearance | pH |
|---|---|---|---|---|
| Initial | 4.90 | 60,000 | Viscous, off white gel | 1.52 |
| 1 month, 40° C. | 4.96 | 74,000 | Viscous, off white gel | 1.45 |
| 1 month, 25° C. | 4.88 | 64,000 | Viscous, off white gel | 1.55 |

[1]RV viscometer, S14 spindle, 6R small sample adaptor, 0.6 rpm.

The assay, appearance, and pH for FA Gel 2 shows no significant change after 1 month at 25 or 40° C. There is a slight increase in viscosity on storage, which is not uncommon for fatty alcohol gels. Their viscosities tend to level off after 1-3 months of storage.

Higher Strength Nu-3 FA Gels: Formulation and Stability

The composition for these gels are shown in Table 7 and the stability results are shown Table 8.

TABLE 7

FA gel compositions. All numbers are % w/w.

| Ingredient | 10% Nu-3 FA Gel | 15% Nu-3 FA Gel | 20% Nu-3 FA Gel |
|---|---|---|---|
| Nu-3 disodium | 10.8 | 16.2 | 21.6 |
| 10% HCl (q.s. to pH 1.5) | 5.0 | 6.6 | 7.8 |
| Crodacol CS 50 NF[1] | 7.25 | 7.25 | 7.25 |
| Cetomacrogol 1000 NF[1] | 1.0 | 1.0 | 1.0 |
| Purified water, USP | q.s. to 100% | q.s. to 100% | q.s. to 100% |

[1]Substution of another vendor's grade of this excipient may cause a significant change in the formulation and is not recommend.

TABLE 8

Stability results for the Nu-3 FA Gels.

| Time point/ storage condition | Assay, % w/w | Viscosity, cP[1] | Appearance[2] | pH |
|---|---|---|---|---|
| Initial | | | | |
| 10% | 10.3 | 63,500 | Conforms | 1.45 |
| 15% | 14.6 | 65,200 | Conforms | 1.52 |
| 20% | 19.9 | 71,000 | Conforms | 1.59 |
| 1 month/40° C. | | | | |
| 10% | 10.2 | 85,600 | Conforms | 1.53 |
| 15% | 14.7 | 89,000 | Conforms | 1.48 |
| 20% | 20.1 | 84,400 | Conforms | 1.63 |
| 1 month/25° C. | | | | |
| 10% | 10.1 | 66,900 | Conforms | 1.44 |
| 15% | 14.6 | 69,000 | Conforms | 1.51 |
| 20% | 19.8 | 72,400 | Conforms | 1.55 |

[1]RV viscometer, S14 spindle, 6R small sample adaptor, 0.6 rpm.
[2]Off-white to tan viscous gel The assay, appearance, and pH for FA gels with 10-20% Nu-3 shows no significant change after 1 month at 25 or 40° C. There is a slight increase in viscosity on storage, which is not uncommon for fatty alcohol gels. Their viscosities tend to level off after 1-3 months of storage.

Example 7: Evaluation of Efficacy of a Bisphosphocin in a *Staphylococcus aureus*-Induced Murine Dermal Infection Model Animals and Husbandry Female SKH1 mice ordered from Charles River Laboratories are acclimated to housing conditions and handled in accordance with Animal Use Protocol (AUP) number TP-18. The animals are acclimated for a minimum of 24 hours prior to bacterial challenge and are 6-8 weeks old on Day 0 of the experiment. Only animals deemed healthy are included in this study. Animals are fed irradiated Teklad Global Rodent Diet 2918 and water ad libitum. Mice are housed in static cages with irradiated Teklad ⅛" corn cob bedding 7902 inside bioBubble® Clean Rooms that provide H.E.P.A. filtered air into the bubble environment at 100 complete air changes per hour. All treatments and infectious challenges are carried out in a BSL2 surgical suite. The environment is controlled to a temperature range of 74°±4° F. and a humidity range of 30-70%. Treatment groups are identified by cage card. All procedures carried out in this experiment are conducted in compliance with the laws, regulations, and guidelines of the National Institutes of Health and with the approval of the TransPharm Animal Care and Use Committee.

Bacterial Cultures

The bacterial strain used in this study is a methicillin resistant *Staphylococcus aureus* strain USA300 (TPPS 1056), procured from the laboratory of Barry Kreiswirth (Public Health Research Institute Center, New Jersey Medical School).

Skin Preparation

On Day 0 immediately prior to infection, each mouse is anesthetized using an isoflurane induction chamber and the dorsal area received 7-10 applications and removals of Nexcare™ (3M) surgical tape in order to remove the outermost epidermal layer of skin.

Challenge

The organism is grown overnight at 37° C. in ambient atmosphere on trypticase soy agar plates supplemented with 5% sheep blood cells. On the day of challenge (Day 0), cultures are aseptically swabbed and transferred to culture tubes of TSB. The cultures are grown in a 37° C. water bath until the optical density reaches approximately 0.65 at 600 nm, providing an undiluted bacterial concentration of approximately 109 colony forming units (CFU)/mL. The cultures are then diluted to provide a challenge inoculate of 6.0 $\log_{10}$ CFU per mouse in a volume of 100 μL. Inoculum count is estimated before inoculation by optical density and confirmed after inoculation by dilution and back count.

Immediately following tape stripping, each animal receives a topical application with approximately 6.0 $\log_{10}$ CFU per mouse in a volume of 100 μL spread in an area approximately 0.75"×0.75". Challenge is allowed to dry slightly before mice are brought out of anesthesia. The final CFU count from the challenge suspension determined that 5.6 $\log_{10}$ CFU per mouse is delivered. Instillation of the bacterial challenge constitutes time 0 hour for the study.

Formulation and Dosing

A 10% (100 mg/mL) solution of Nu-3 is prepared in a fatty alcohol-based gel. Hydrocholoric acid is used to adjust the solution to pH 1.5.

Four hours following challenge, mice receive a topical application of test article or vehicle gel to the dorsal area previously stripped and inoculated with bacteria. The gel is spread evenly using a sterile loop. Control animals do not receive treatment. Mice are housed individually following treatment until time of harvest.

Endpoint Analysis

Mice are harvested at designated time points based upon the study. Four mice are harvested from each group at each time point.

Following euthanasia, a section of excised skin approximately 0.5"×0.5" is aseptically removed from the infected/treated area and transferred to vials with 2.0 mL of sterile water and weighed. Tissues are allowed to set at room temperature for 10 minutes. Tissue pH is measured using litmus paper and recorded. Following pH measurement, tissues are homogenized using a bead beater. The homogenate is serially diluted from neat to 10−7 in PBS and plated in duplicate 5 μL spots onto trypticase soy agar plates supplemented with 5% sheep blood cells. 100 μL of the undiluted (neat) homogenate is plated for each sample. Plates are incubated overnight at 37° C. in ambient atmosphere. Colony forming units (CFU) are tabulated for each treatment per gram of tissue.

Results and Discussion

None of the mice displayed any acute adverse events associated with the treatments. None of the mice succumbed to the infection or showed signs of morbidity, which could be attributed to penetration of the infection into the circulatory system or deep tissue. No groups displayed adverse signs beyond those expected for mice which have received a superficial bacterial infection.

The baseline bacterial burden of the untreated group (Group 1) is 6.94 $\log_{10}$ CFU at 5 hours post-challenge and 8.14 $\log_{10}$ CFU at 12 hours post-challenge. Group 2, which was administered vehicle, did not demonstrate significant changes when compared to the untreated group. Group 3, which received Nu-3, showed significant decreases in CFU burden at 5 and 12 hours post-challenge when compared to that of untreated control animals. Group 3 also showed significant decreases in CFU burden at all harvest time points when compared to vehicle-treated animals.

Together, these data demonstrate that *Staphylococcus aureus* establishes a robust dermal infection. Topical administration of Nu-3 significantly decreases bacterial burden at 5 and 12 hours post-challenge when compared to untreated controls and at all time points when compared to the vehicle-treated group.

While embodiments have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A formulation comprising:
   from about 1% to about 20% (weight/weight) of a Nu-3, or a pharmaceutically acceptable salt thereof;
   from about 1% to about 10% (weight/weight) of a fatty alcohol thickening agent;
   from about 0.5% to about 5% (weight/weight) of a nonionic polymer emulsifier; and
   from about 65% to about 97.5% (weight/weight) of a diluent,
   wherein the formulation is a gel formulation having a pH of about pH 1 to about pH 3.

2. The formulation of claim 1, wherein the Nu-3 is present in the formulation in an amount from about 1% to about 15% (weight/weight).

3. The formulation of claim 1, wherein the Nu-3 is present in the formulation in an amount from about 5% to about 15% (weight/weight).

4. The formulation of claim 1, wherein the fatty alcohol thickening agent is present in the formulation in an amount from about 2% to about 8% (weight/weight).

5. The formulation of claim 1, wherein the nonionic polymer emulsifier is present in the formulation in an amount from about 0.5% to about 5% (weight/weight).

6. The formulation of claim 1, wherein the diluent is selected from the group consisting of water, glycerol, mannitol, saline, phosphate buffered saline, and combinations thereof.

7. The formulation of claim 6, wherein the diluent is water.

8. The formulation of claim 1, wherein the fatty alcohol thickening agent is selected from the group consisting of cetyl alcohol, lauryl alcohol, stearyl alcohol, cetostearyl alcohol, myristyl alcohol, docosanol alcohol, oleyl alcohol, and combinations thereof.

9. The formulation of claim 8, wherein the fatty alcohol thickening agent is cetostearyl alcohol.

10. The formulation of claim 9, wherein the cetostearyl alcohol is present in the formulation in an amount from about 2% to about 10% (w/w).

11. The formulation of claim 1, wherein the nonionic polymer is selected from the group consisting of polysorbate 20, polysorbate 60, polysorbate 80, ceteareth-12, ceteareth-30, ceteth-10, ceteth-20, steareth-10, steareth-20, steareth-40, steareth-100, ceteareth-20, and combinations thereof.

12. The formulation of claim 11, wherein the nonionic polymer emulsifier is ceteareth-20.

13. The formulation of claim 12, wherein the ceteareth-20 is present in the formulation in an amount greater than about 0.5% (w/w).

14. The formulation of claim 12, wherein the ceteareth-20 is present in the formulation in an amount of about 0.5% to about 5% (w/w).

15. The formulation of claim 1, wherein the formulation is adapted for topical administration.

16. The formulation of claim 1, wherein the formulation is adapted for treating an infection in a patient.

17. The formulation of claim 16, wherein the infection is selected from the group consisting of an infection of an ulcer, an infection of a wound, and an otitis externa infection.

18. The formulation of claim 16, wherein the infection is selected from the group consisting of acne vulgaris, onychomycosis, conjunctivitis, oral mucositis, an infection of a mucosal surface, a vaginal infection, and combinations thereof.

19. The formulation of claim 16, wherein the infection is an infection of a diabetic foot ulcer or a complicated venous leg ulcer.

20. The formulation of claim 16, wherein the infection is an infection of a burn wound.

21. The formulation of claim 16, wherein the infection is an infection of a wound or ulcer.

22. The formulation of claim 16, further comprising at least one additional active ingredient.

23. The formulation of claim 16, wherein the patient is a human.

* * * * *